US012642819B2

(12) United States Patent
Britton et al.

(10) Patent No.: US 12,642,819 B2
(45) Date of Patent: Jun. 2, 2026

(54) COMPOSITIONS AND METHODS FOR TREATING INFLAMMATORY BOWEL DISEASE

(71) Applicant: Icahn School of Medicine at Mount Sinai, New York, NY (US)

(72) Inventors: Graham J. Britton, New York, NY (US); Jeremiah J. Faith, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 693 days.

(21) Appl. No.: 17/786,123

(22) PCT Filed: Dec. 19, 2020

(86) PCT No.: PCT/US2020/066262
§ 371 (c)(1),
(2) Date: Jun. 16, 2022

(87) PCT Pub. No.: WO2021/127598
PCT Pub. Date: Jun. 24, 2021

(65) Prior Publication Data
US 2023/0046662 A1     Feb. 16, 2023

Related U.S. Application Data

(60) Provisional application No. 62/951,167, filed on Dec. 20, 2019.

(51) Int. Cl.
| | |
|---|---|
| *A61K 35/74* | (2015.01) |
| *A61K 35/742* | (2015.01) |
| *A61K 35/744* | (2015.01) |
| *A61K 35/745* | (2015.01) |
| *A61K 35/747* | (2015.01) |
| *A61P 1/00* | (2006.01) |
| *G01N 33/50* | (2006.01) |
| *A61K 35/00* | (2006.01) |

(52) U.S. Cl.
CPC ............ *A61K 35/74* (2013.01); *A61K 35/742* (2013.01); *A61K 35/744* (2013.01); *A61K 35/745* (2013.01); *A61K 35/747* (2013.01); *A61P 1/00* (2018.01); *G01N 33/5091* (2013.01); *A61K 2035/115* (2013.01)

(58) Field of Classification Search
CPC .... A61K 35/74; A61K 35/742; A61K 35/744; A61K 35/745; A61K 35/747; A61K 2035/115
See application file for complete search history.

(56) References Cited

FOREIGN PATENT DOCUMENTS

| | | |
|---|---|---|
| CN | 112739376 | 4/2021 |
| EP | 3 895 710 | 10/2021 |
| JP | 2013-537531 | 10/2013 |
| JP | 2014-507481 | 3/2014 |
| WO | WO 2016/209806 | 12/2016 |
| WO | WO 2019/209640 | 10/2019 |
| WO | WO 2019/227085 | 11/2019 |

OTHER PUBLICATIONS

H. Kwon, C. Lee, J. So, C. Chae, J. Hwang, A. Sahoo, J.H. Nam, J.H. Rhee, K. Hwang, & S. Im, Generation of regulatory dendritic cells and CD4+Foxp3+ T cells by probiotics administration suppresses immune disorders, Proc. Natl. Acad. Sci. U.S.A. 107 (5) 2159-2164, (2010). (Year: 2010).*
Ozerlat, I. ROR blockers inhibit TH17 cells. Nat Rev Neurol 7, 303 (2011). https://doi.org/10.1038/nrneurol.2011.75 (Year: 2011).*
Guo NH, Fu X, Zi FM, Song Y, Wang S, Cheng J. The potential therapeutic benefit of resveratrol on Th17/Treg imbalance in immune thrombocytopenia purpura. Int Immunopharmacol. Aug. 2019;73:181-192. doi: 10.1016/j.intimp.2019.04.061. Epub May 16, 2019. PMID: 31102993. (Year: 2019).*
IPRP, "International Preliminary Report of Patentability in PCT/US20/066262", Jun. 30, 2022, 10 Pages.
"International Search Report and Written Opinion in International Application No. PCT/US2020/066262, filed Dec. 19, 2020", May 6, 2021, 18 pages.
Britton, Contijoch EJ, et al., "Microbiotas from Humans with Inflammatory Bowel Disease Alter the Balance of Gut TH17 and RORgammat+ Regulatory T Cells and Exacerbate Colitis in Mice Immunity", Jan. 15, 2019; vol. 50, No. 1, pp. 212-224, p. 213, col. 1, para 3; p. 220, col. 2, para 1; Fig. 3; Fig. 5A; p. e3, para 2; p. 216, col. 2, para 1; p. e3, para 1, p. 219, col. 2, para 2; p. 212, summary; Table 1.
"Japanese Office Action mailed Jul. 31, 2023 in JP Application No. 2022-538098", 16 pages.
"Office Action in Canadian Application No. 3162387", Jun. 14, 2023, 5 pages.
Britton, et al., "Microbiotas from Humans with Inflammatory Bowel Disease Alter the Balance of Gut Th17 and RORγt+ Regulatory T Cells and Exacerbate Colitis in Mice", Immunity, Jan. 15, 2019, 50, 212-224.
"Communication Pursuant to Rules 70(2) and 70a(2) EPC in EP Application No. 20904321.6", Jan. 9, 2024, 1.
"Examination Report in Australian Application No. 2020407659", Mar. 13, 2024, 4 pages.
"Extended European Search Report in EP Application No. 20904231.6", Dec. 22, 2023, 11 pages.
"First Office Action In Chinese Application No. 202080097355.0", Jan. 20, 2025, 42 pages.
B-H Yang, et al., "Foxp3+ T cells expressing ROR[gamma]t represent a stable regulatory T-cell effector lineage with enhanced suppressive capacity during intestinal inflammation", Mucosal Immunology, vol. 9, No. 2, Aug. 26, 2015 (Aug. 26, 2015), pp. 444-457, XP055706437, New York, ISSN: 1933-0219, DOI: 10.1038/mi.2015.74, 14 pages.

(Continued)

*Primary Examiner* — Melenie L Gordon
*Assistant Examiner* — John Paul Selwanes
(74) *Attorney, Agent, or Firm* — IP Spring

(57) ABSTRACT

The present invention provides methods of diagnosing, treating, and monitoring the progression of inflammatory bowel disease in a subject, including, for example, by monitoring RORγt⁺Th or RORγt⁺Treg cell levels and treating the subject accordingly.

6 Claims, 28 Drawing Sheets

Specification includes a Sequence Listing.

(56)                    References Cited

OTHER PUBLICATIONS

De Jong Renske J., et al., "Defining Dysbiosis in Inflammatory Bowel Disease", Immunity, vol. 50, No. 1, Jan. 1, 2019 (Jan. 1, 2019), pp. 8-10, XP93111819, Amsterdam, NL ISSN: 1074-7613, DOI: 10.1016/j.immuni.2018.12.028, 3 pages.

Galvez Julio, et al., "Role of Th17 Cells in the Pathogenesis of Human IBD", ISRN Inflammation, vol. 2014, Mar. 25, 2014 (Mar. 25, 2014), pp. 1-14, XP93111346, ISSN: 2090-8695, DOI: 10.1155/2014/928461 Retrieved from the Internet: URL:http://downloads.hindawi.com/archive/2014/928461.XML>, 14 pages.

Graham J. Britton, et al., "Inflammatory bowel disease microbiotas alter gut CI) 4 T-1 cell homeostasis and drive colitis in mice", BIORXIV, Mar. 6, 2018 (Mar. 6, 2018), pp. 1-18, XP55648866, DOI: 10.1101/276774, 18 pages.

Graham J. Britton, et al., "Defined microbiota transplant restores Th17/ROR[gamma]t + regulatory T cell balance in mice colonized with inflammatory bowel disease microbiotas", Proceedings of the National Academy of Sciences, vol. 117, No. 35, Aug. 18, 2020 (Aug. 18, 2020), pp. 21536-21545, XP93111340, ISSN: 0027-8424, DOI: 10.1073/pnas.1922189117, 10 pages.

M. Lochner, et al., "Restricted Microbiota and Absence of Cognate TCR Antigen Leads to an Unbalanced Generation of Th17 Cells", The Journal of Immunology, vol. 186, No. 3, Feb. 1, 2011 (Feb. 1, 2011), pp. 1531-1537, XP055341493, US ISSN: 0022-1767, DOI: 10.4049/jimmunol.1001723, 8 pages.

"Communication pursuant to Article 94(3) EPC in EP Application No. 20904231.6", Mar. 24, 2025, 4 pages.

* cited by examiner

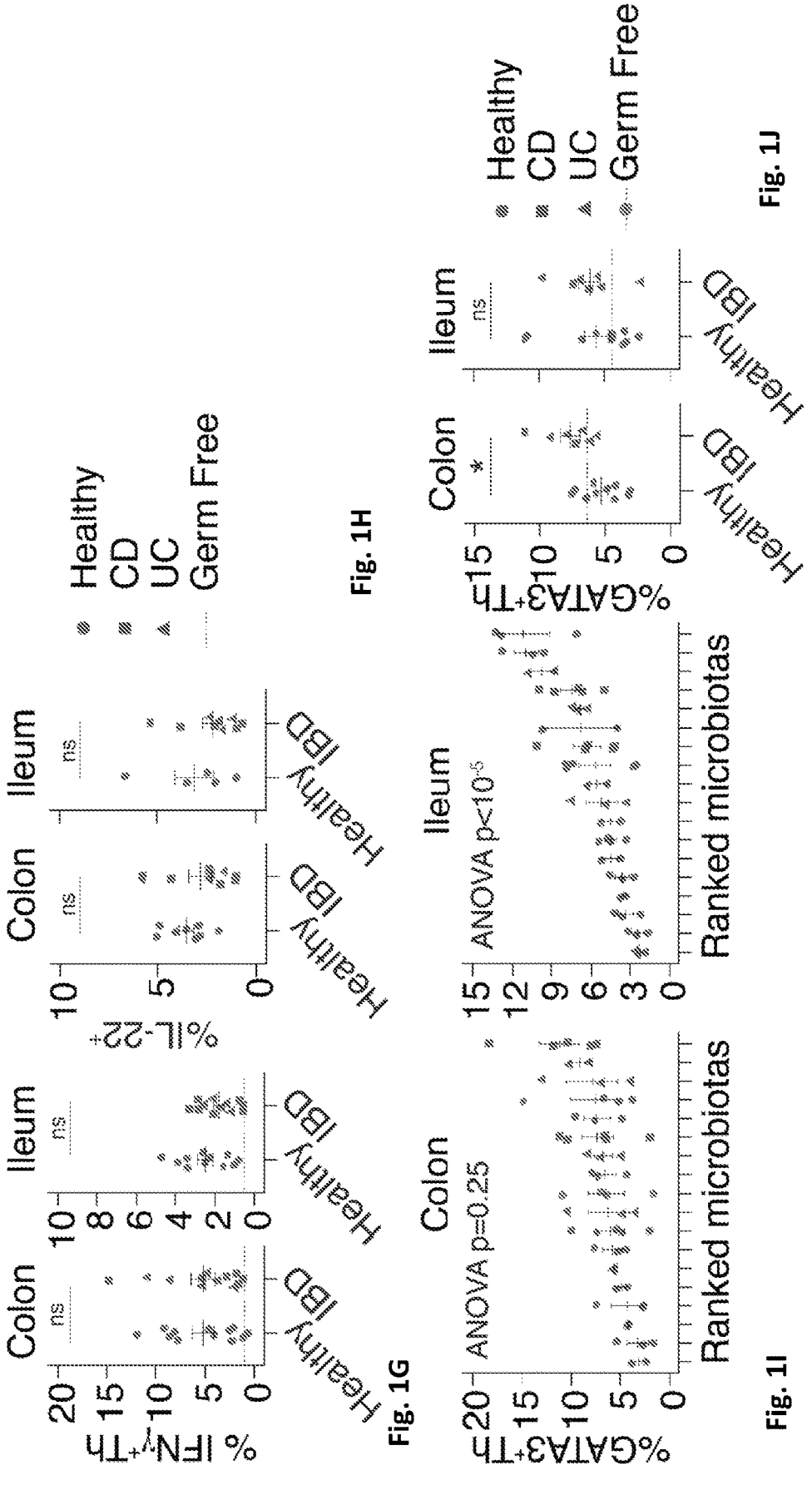

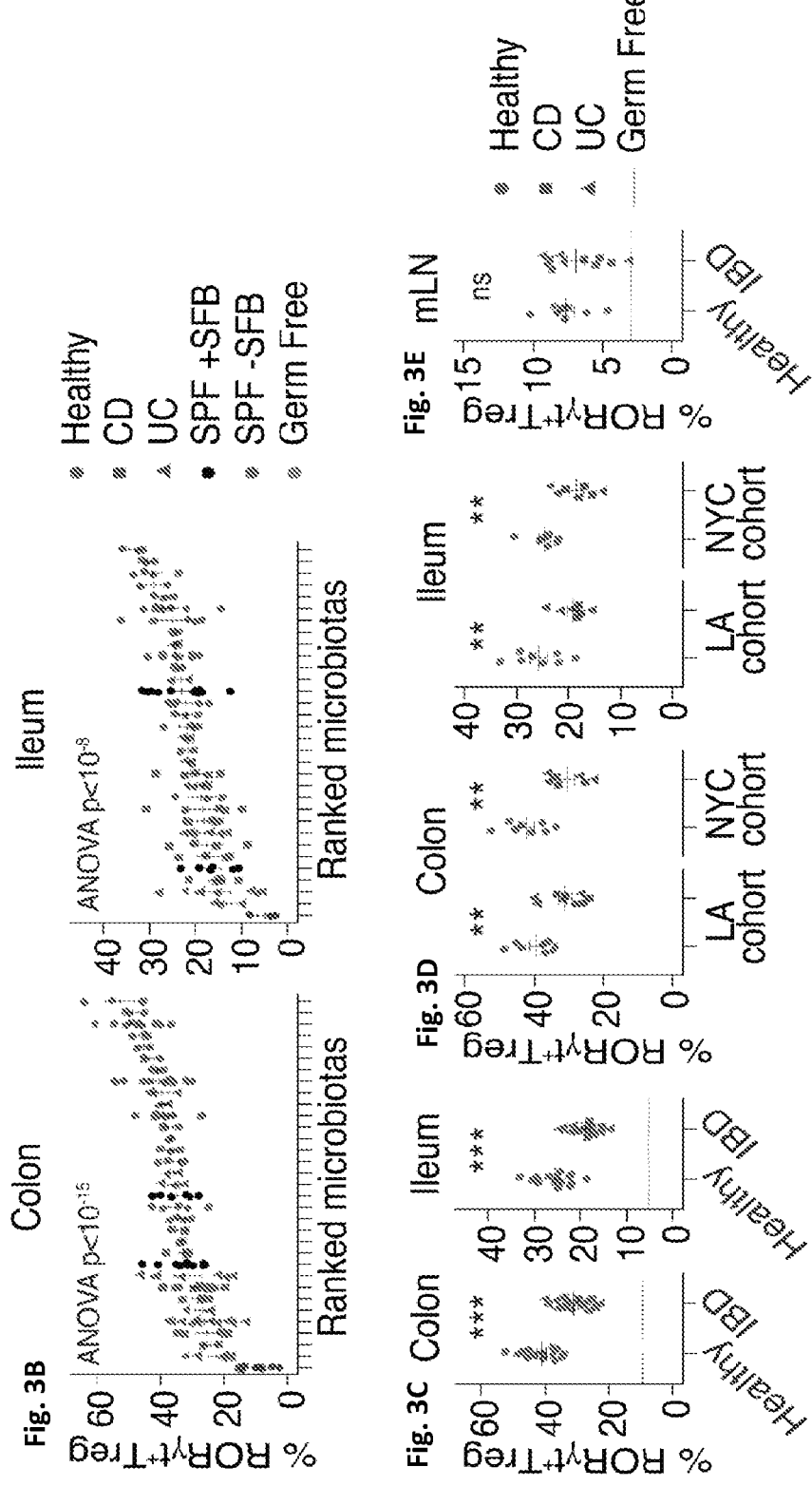

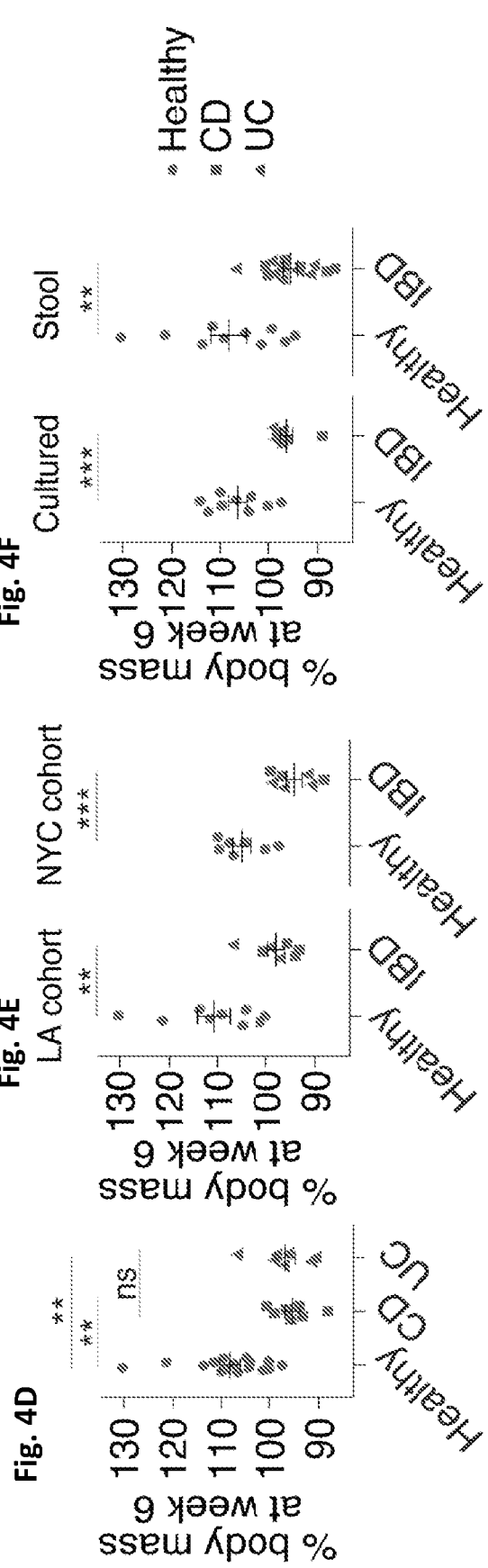

RORγt+ Th          AUC: 0.71

RORγt+ Treg          AUC: 0.92

TCT week 6          AUC: 0.93

RORγt+ Treg
+
TCT week 6          AUC: 0.95

| Microbiota | T cell donor |
|------------|--------------|
| ● HD2021 | FoxP3$^{Cre}$ x RORgt$^{FL/WT}$ |
| ● HD2021 | FoxP3$^{Cre}$ x RORgt$^{FL/FL}$ |
| ● UC1024 | FoxP3$^{Cre}$ x RORgt$^{FL/WT}$ |

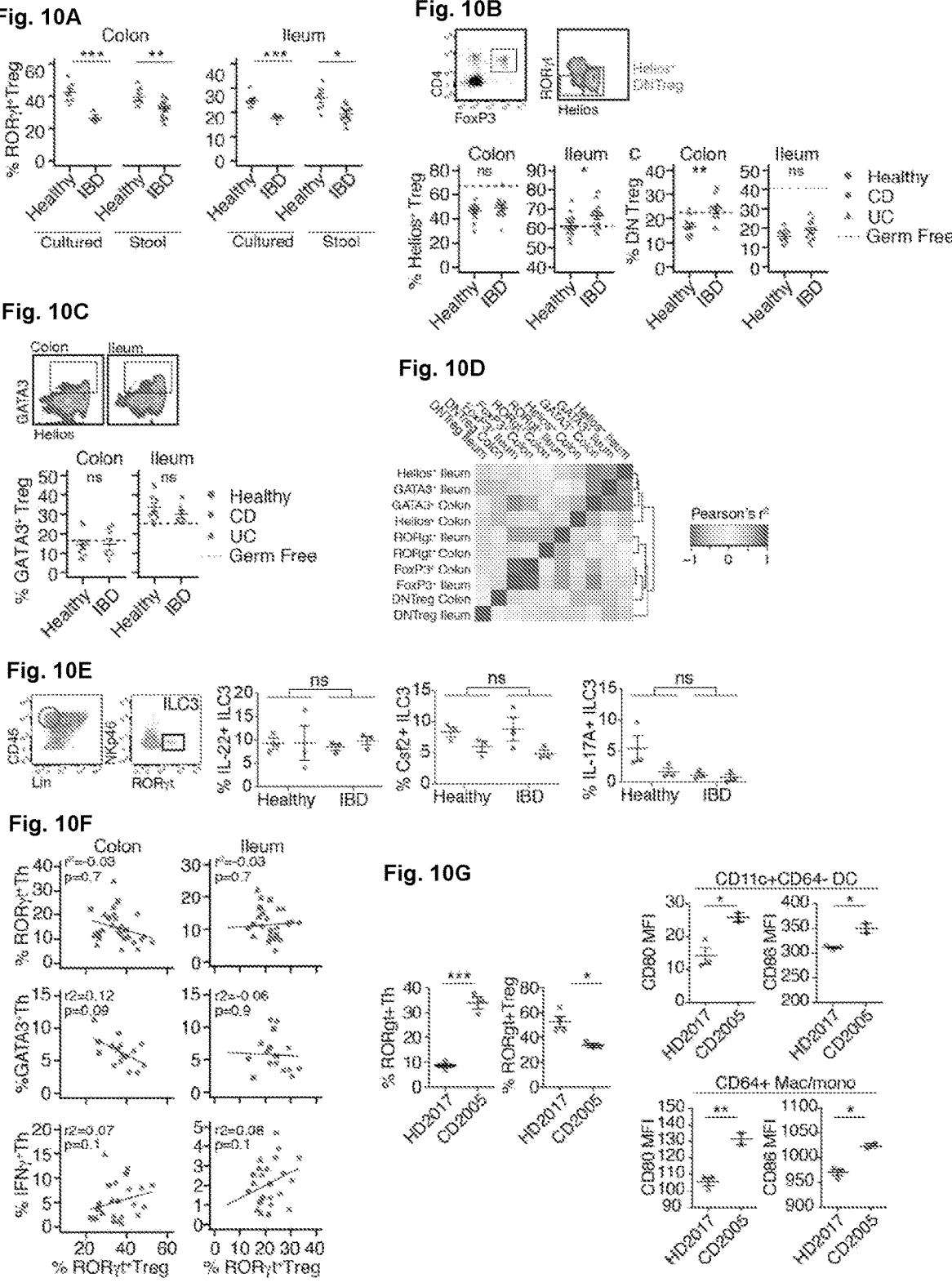

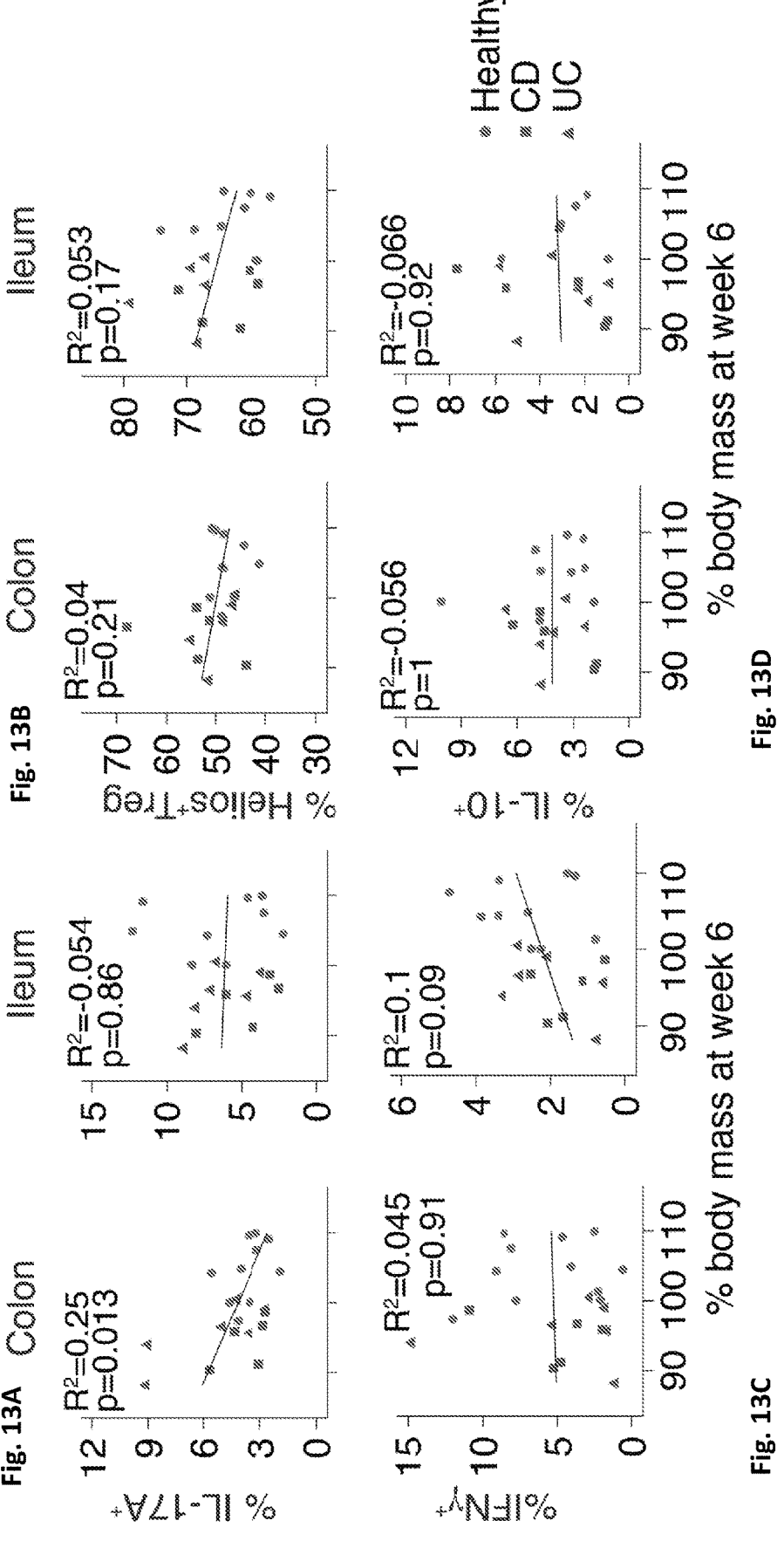

COMPOSITIONS AND METHODS FOR TREATING INFLAMMATORY BOWEL DISEASE

STATEMENT REGARDING FEDERALLY SPONSORED RESEARCH

This invention was made with government support under NIGMS GM108505 awarded by NIH. The government has certain rights in the invention.

SEQUENCE LISTING

The instant application contains a "lengthy" Sequence Listing which has been submitted via CD-R in lieu of a printed paper copy, and is hereby incorporated by reference in its entirety. Said CD-R, recorded on Jun. 14, 2022, are labeled "CRF", "Copy 1" and "Copy 2", respectively, and each contains only one identical 280,467,694 bytes file (MS-0006-01-US-NP_SL.txt), which file was created on Dec. 17, 2019.

RELATED APPLICATIONS

This application is a § 371 national stage of PCT International Application No. PCT/US20/66262, filed Dec. 19, 2020, which claims the benefit of U.S. Provisional Patent Application Ser. No. 62/951,167, filed Dec. 20, 2019, which is encorporated by reference in its entirety.

BACKGROUND

The mammalian gastrointestinal (GI) tract harbors a diverse microbial community that is usually maintained in symbiotic balance. Interactions between microbes within the microbial populations, and between the microbes and the host, affect both the host and the internal microbial community. For example, a majority of the mammalian immune system is directed at the GI tract. This may affect the internal microbial community structure, by eliminating some microbes and enabling the expansion of others. Even the host diet shapes the GI microbial community often by introducing new microbes, benefitting some microbes, or inhibiting others.

A healthy GI microbiome also benefits the host. It can render the host resistant to colonization by a broad spectrum of pathogens, provide immune stimulation, promote maintenance of a healthy gut epithelium, and provide essential nutrients such as vitamin K for absorption. In some individuals, this symbiotic balance is disrupted. This state can lead to disruption of microbial functions and lead to increased susceptibility to pathogens, induction of inflammatory signaling cascades that result in autoimmunity, and disruption of nutrient absorption. Consequently, the GI microbiome is a significant element in the pathogenesis of many diseases and disorders. Some patients become more susceptible to pathogenic infections after the use of broad-spectrum antibiotics that disrupt the normal intestinal microbiota flora. Many of these diseases and disorders, such as inflammatory bowel disease (IBD) are chronic conditions that significantly decrease a patient's quality of life and can be ultimately fatal.

IBD describes a variety of intestinal disorders, including Crohn's disease (CD) and ulcerative colitis (UC), which are all characterized by dysregulated GI immune responses and localized inflammatory signals in affected patients. Numerous animal models suggest the microbial strains that constitute the gut microbiota play a crucial role in shaping the immune system, consequentially influencing host susceptibility to autoimmunity, inflammatory disease, and infection. See, e.g., K. Atarashi et al. (2017) *Science* 358, 359-365; K. Atarashi et al. (2011) *Science* 331, 337-341; Ivanov, II, et al. (2009) *Cell* 139, 485-498; A. Chudnovskiy et al. (2016) *Cell* 167, 444-456 e414. And genetic defects in microbial handling are implicated in disease. L. Jostins, et al. (2012) *Nature* 491, 119-124.

Therefore, interventions targeting the microbiota are potentially a path to treatment of IBD. P. Moayyedi, et al. (2015) *Gastroenterology* 149, 102-109; S. Paramsothy, et al. (2017), *Lancet* 389, 1218-1228. Recent research has focused on the induction of certain immune cell populations in the GI as markers of IBD. Some studies have correlated specific bacteria with differentiation of Th17 cells in mouse models of IBD. Ivanov, II, et al., (2008) *Cell Host Microbe,* 4 (4): 337; and Tan, T. G., et al., (2016) *PNAS USA,* 113(50): E8141. Another shows that IgA coated *E. coli* induce inflammation and Th17 accumulation in the gut of Crohn's disease patients. Viladomiu, M., et al., (2017) *Sci Transl Med,* 9(376). An antibody that inhibits IL-23, a cytokine required for differentiation of Th17 cells, leads to clinical improvement in individuals with Crohn's disease. Sands, et al. (2017) *Gastroenterology* 153(1):77-86. One study has also shown that induction of Th17 cells by gut microbiota provide protection from gut pathogens. Ivanov, II, et al., (2009) *Cell* 139(3): 485.

While these studies provide suggestions that one immune signal may be correlated with IBD in affected individuals, there is a need in the art for improved methods for detecting, staging, and treating subjects with IBD based on multiple immune markers associated with IBD. There is also a need for identifying therapeutic agents for modulating the effects of these immunogenic signals in the GI of individuals afflicted with IBD. The present disclosure fulfills these needs by identifying for the first time multiple microbiota-induced T-cell populations that are correlated with IBD disease and associated with its progression.

SUMMARY OF THE DISCLOSURE

The present disclosure relates generally to diagnosing, treating, and monitoring the progression of inflammatory bowel disease in a subject, including, for example, by monitoring RORγt⁺Th or RORγt⁺Treg cell levels and treating a subject accordingly. The present disclosure also relates to a method for inhibiting proliferation or accumulation of RORγt⁺Th cells or modulating an immune or inflammatory response. The present disclosure also relates to a method for inducing proliferation or accumulation of RORγt⁺Treg cells or modulating an immune or inflammatory response. Such methods may include reduction of inflammation caused by RORγt⁺Th cells or enhancing the protective effect of RORγt⁺Treg cells in the gastrointestinal tract via a drug, vaccine, probiotic, or other means. Diagnosis and monitoring can be achieved by tracking biomarkers in the subject that are associated with the specific microbial strain identified.

BRIEF DESCRIPTION OF THE FIGURES

FIG. 1A-J. The figures show that IBD-associated microbiotas enhance induction of gut RORγt+ Th compared to healthy donor microbiotas in gnotobiotic mice.

FIG. 3A-G. The figures show that healthy donor microbiotas specifically enhance induction of gut RORγt+ Treg compared to IBD-associated microbiotas.

FIG. 4A-I. The figures show that IBD-associated microbiotas transmit enhanced colitis severity to susceptible mice.

FIG. 10A-G. The figures show that healthy donor microbiotas specifically enhance induction of gut RORγt+Treg compared to IBD-associated microbiotas.

FIG. 13A-D. The figures show a relationship between homeostatically-induced T cell populations and colitis severity.

DEFINITIONS

Figures 1A, 1B:
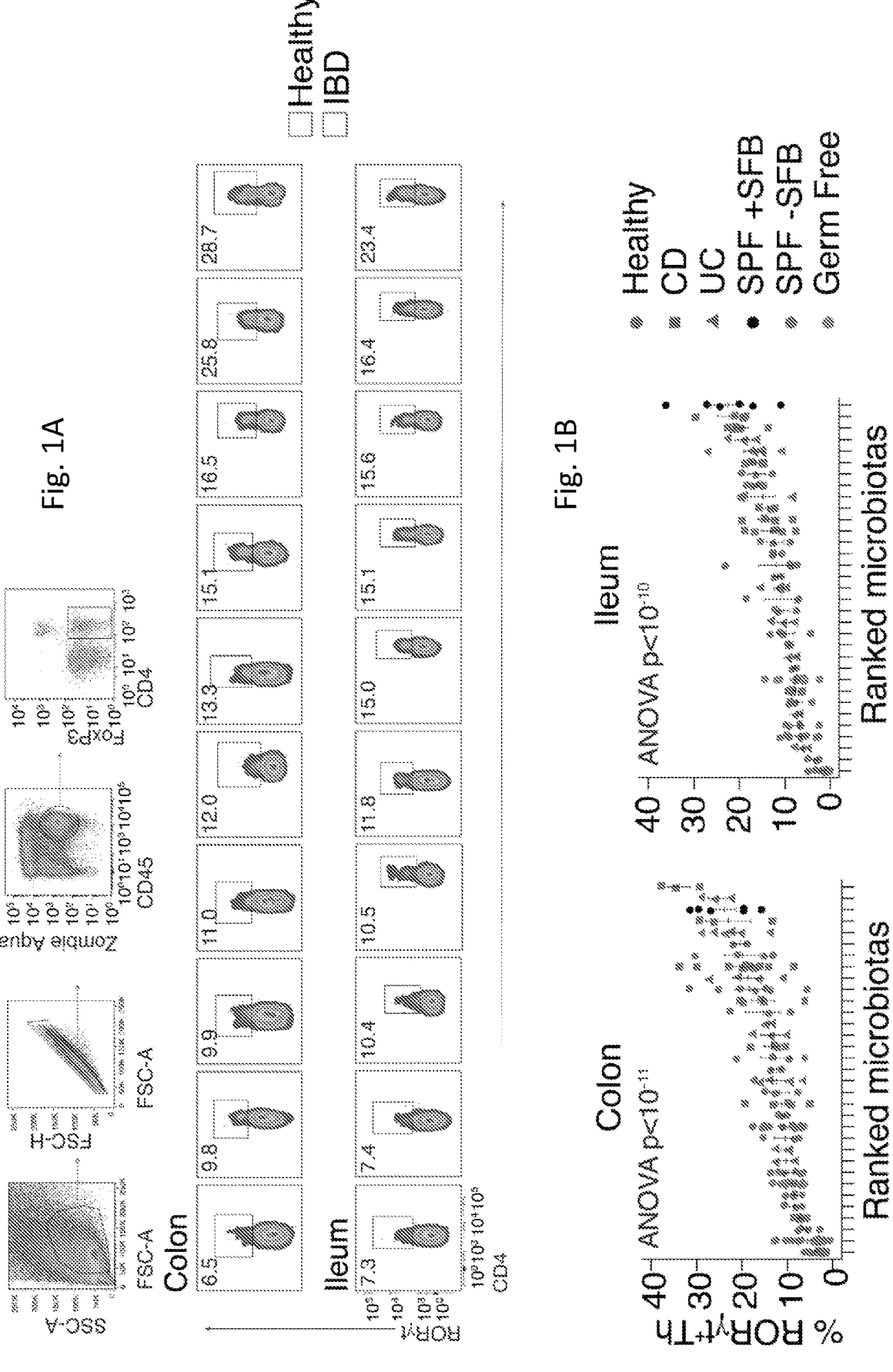

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular.

As used herein, the terms "comprising" (and any form of comprising, such as "comprise," "comprises," and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or"

clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the term "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

The term "about" is used herein to mean within the typical ranges of tolerances in the art. For example, "about" can be understood as about 2 standard deviations from the mean. According to certain embodiments, when referring to a measurable value such as an amount and the like, "about" is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value as such variations are appropriate to perform the disclosed methods. When "about" is present before a series of numbers or a range, it is understood that "about" can modify each of the numbers in the series or range.

As used herein, the term "individual" in the present disclosure is not particularly limited, and examples thereof may include humans, mice, rats, cattle, horses, pigs, sheep, monkeys, dogs, and cats.

As used herein, the term "therapeutic composition" according to the present disclosure may be in the form of a vaccine, adjuvant, biological, pharmaceutical composition, probiotic, food, beverage, fecal transplant, complex microbial or fecal sample, bacterial strain, mixture of bacterial strains, a reagent used in an animal model, or a combination of such ingredients. The vaccine, adjuvant, biological, pharmaceutical composition, probiotic, food, beverage, or reagent, or combinatorial product can have the effect of reducing or eliminating IBD in a subject. The therapeutic compositions according to the present disclosure can also have the effect of stimulating or enhancing the differentiation, accumulation, or proliferation of RORγt⁺Treg cells or of reducing the differentiation, accumulation, or proliferation of RORγt⁺Th cells in a subject or of stimulating the immune response in a subject. Administration of such therapeutic compositions may be oral, buccal, parenteral, rectal, or via fecal transplantation.

The term "IBD" in the present disclosure includes gastrointestinal disorders such as inflammatory bowel disease (IBD), ulcerative colitis, and Crohn's disease.

As used herein, the term "RORγt⁺Th" means CD4⁺ αβ T cells that are RORγt positive and FoxP3 negative.

As used herein, the term "RORγt⁺Treg cells" means CD4⁺ αβ T cells that co-express FoxP3 and RORγt markers. They may also be identified by co-expression of FoxP3 and Neuropilin 1.

As used herein, the phrase "reducing or eliminating differentiation, accumulation, or proliferation of RORγt⁺Th cells" in the present disclosure includes an effect of reducing or inhibiting the differentiation of immature T cells into RORγt⁺Th cells, which differentiation leads to the proliferation or the accumulation of RORγt⁺Th cells. In addition, the meaning of the "reducing or eliminating differentiation, accumulation, or proliferation of RORγt⁺Th cells" in the present disclosure includes in-vivo effects, in vitro effects, and ex vivo effects. Accordingly, all of the following effects are included: reducing or inhibiting in vivo proliferation or accumulation of RORγt⁺Th cells in the gut through administration or ingestion of a therapeutic composition that inhibits IBD; reducing or inhibiting proliferation or accumulation of RORγt⁺Th cells by preventing a physiologically active substance to act on cultured RORγt⁺Th cells; and reducing or inhibiting proliferation or accumulation of RORγt⁺Th cells that are collected from a living organism and that are intended to be subsequently reintroduced into that organism or introduced into another organism, by preventing a physiologically active substance from acting on the RORγt⁺Th cells.

As used herein, the phrase "stimulating or enhancing the differentiation, accumulation, or proliferation of RORγt⁺ Treg cells" in the present disclosure includes an effect of increasing or stimulating the differentiation of immature T cells into RORγt⁺Treg cells, which differentiation leads to the proliferation or the accumulation of RORγt⁺Treg cells. In addition, the meaning of the "stimulating or enhancing the differentiation, accumulation, or proliferation of RORγt⁺ Treg cells" in the present disclosure includes in-vivo effects, in vitro effects, and ex vivo effects. Accordingly, all of the following effects are included: stimulating or enhancing in vivo proliferation or accumulation of RORγt⁺Treg cells in the gut through administration or ingestion of a therapeutic composition that inhibits IBD; increasing or enhancing proliferation or accumulation of RORγt⁺Treg cells by allowing or enhancing a physiologically active substance to act on cultured RORγt⁺Treg cells; and increasing or enhancing proliferation or accumulation of RORγt⁺Treg cells that are collected from a living organism and that are intended to be subsequently reintroduced into that organism or introduced into another organism, by allowing or enhancing a physiologically active substance to act on the RORγt⁺Treg cells.

DETAILED DESCRIPTION

In the following description, reference is made to certain formulations and specific embodiments that form a part hereof. The illustrative embodiments described in the detailed description and claims are not meant to be limiting. Other embodiments may be utilized, and other changes may be made, without departing from the scope of the present subject matter. Aspects of the present disclosure, can be arranged, substituted, combined, separated, and designed in a wide variety of different configurations, all of which are contemplated herein.

References in the specification to "one embodiment", "an embodiment", "an example embodiment" or "some embodiments," etc. indicate that the embodiments described may include a particular feature or characteristic, but every embodiment may not necessarily include the particular feature, structure, or characteristic. Moreover, such phrases are not necessarily referring to the same embodiment. Further, when a particular feature, structure, or characteristic is described in connection with an embodiment, such feature, structure, or characteristic may be achieved in connection with other embodiments whether or not explicitly described.

The present disclosure identifies for the first time multiple immunogenic cell types that can serve as markers for IBD. One aspect of the present disclosure provides a specific T-cell marker that is positively correlated with IBD. Another aspect of the present disclosure provides a specific T-cell marker that is inversely correlated with IBD.

One aspect of the present disclosure provides biological markers for staging or tracking IBD. Another aspect of the present disclosure provides a biological marker and a method for treating IBD. Another aspect of the present disclosure provides a method of screening for compositions and methods to treat or prevent IBD.

One aspect of the present disclosure provides a therapeutic composition for modulating an immune response in a subject. Another aspect of the present disclosure provides a method for treating or preventing at least one disease or condition selected from infectious diseases, cancer, and autoimmune diseases.

The disclosure provides a method in which the absolute amount or the ratio of RORγt⁺Th cell levels in the GI and gut lymph nodes of an individual with IBD is determined and can be compared with the baseline value of the amount of RORγt⁺Th cell levels in the GI of a healthy individual to provide an IBD diagnosis, prognosis, or treatment regimen.

The disclosure provides a method in which the absolute amount or the ratio of RORγt⁺Treg cell levels in the GI and gut lymph nodes of an individual with IBD is determined and can be compared with the baseline value of the amount of RORγt⁺Treg cell levels in the GI of a healthy individual to provide an IBD diagnosis, prognosis, or treatment regimen.

In one embodiment, the disclosure provides a method in which the absolute amount or the ratio of RORγt⁺Th cell levels in the GI and gut lymph nodes of an individual with IBD is determined, and, when a therapeutically active composition is administered to the individual that reduces the ratio or the absolute value of the RORγt⁺Th cell levels in comparison with a base line value in a healthy individual, it is determined that the therapeutically active composition is effective in treating IBD.

In one embodiment, the disclosure provides a method in which the absolute amount or the ratio of RORγt⁺Treg cell levels in the GI and gut lymph nodes of an individual with IBD is determined, and when a therapeutically active composition is administered to the individual that increases the ratio or the absolute value of the RORγt⁺Treg cell levels in comparison with a base line value in a healthy individual, it is determined that the therapeutically active composition is effective in treating IBD.

In one embodiment, the disclosure provides a method in which the absolute amount or the ratio of RORγt⁺Th cell levels and RORγt⁺Treg cell levels in the GI and gut lymph nodes of an individual with IBD is determined, and when a therapeutically active composition is administered to the individual that reduces the ratio or the absolute value of the RORγt⁺Th cell levels or increases the ratio or the absolute value of the RORγt⁺Treg cell levels in comparison with a base line value in a healthy individual, it is determined that the therapeutically active composition is effective in treating IBD.

In one embodiment, the disclosure provides a method in which the absolute amount or the ratio of RORγt⁺Th cell levels and RORγt⁺Treg cell levels in the GI and gut lymph nodes of an individual with IBD is determined, and when a therapeutically active composition is administered to the individual that reduces the ratio or the absolute value of the RORγt⁺Th cell levels and increases the ratio or the absolute value of the RORγt⁺Treg cell levels in comparison with a base line value in a healthy individual, it is determined that the therapeutically active composition is effective in treating IBD.

In one embodiment, the method further comprises measuring the levels of RORγt⁺Th cell levels in the GI and gut lymph nodes of the subject after administration of a therapeutic composition, wherein a decrease in the percentage or absolute number of RORγt⁺Th cell levels in the GI of the subject after administration of the therapeutic composition relative to levels prior to the administration is a positive indicator of enhanced immunosuppression (or immunoregulation). The measurement of the RORγt⁺Th cell levels in the subject's GI can be made with techniques known in the art, such as flow cytometry, immunohistochemistry, or immunofluorescence.

In one embodiment, the method further comprises measuring the levels of RORγt⁺Treg cell levels in the GI and gut lymph nodes of the subject after administration of a therapeutic composition, wherein a decrease in the percentage or absolute number of RORγt⁺Treg cell levels in the GI of the subject after administration of the therapeutic composition relative to levels prior to the administration is a positive indicator of enhanced immunosuppression (or immunoregulation). The measurement of the RORγt⁺Th cell levels in the subject's GI can be made with techniques known in the art, such as flow cytometry, immunohistochemistry, or immunofluorescence.

One embodiment provides a method for diagnosing IBD in a patient by: (a) obtaining a sample from a patient exhibiting symptoms associated with IBD; (b) incubating the sample in a microbe free mammal or in-vitro immune environment; (c) contacting the sample with an antibody that binds to RORγt⁺Th cells; (d) detecting binding of the antibody with RORγt⁺Th cells in the sample; and (e) predicting the presence or assessing status of IBD when the level of RORγt⁺Th cells in the patient is higher than a predetermined level of RORγt⁺Th cells.

One embodiment provides a method for diagnosing IBD in a patient by: (a) obtaining a sample from a patient exhibiting symptoms associated with IBD; (b) contacting the sample with an antibody that binds to RORγt⁺Treg cells; (d) detecting binding of the antibody with RORγt⁺Treg cells in the sample; and (e) predicting the presence or assessing status of IBD when the level of RORγt⁺Treg cells in the patient is higher than a predetermined level of RORγt⁺Treg cells.

One embodiment provides a method for diagnosing IBD in a patient by: (a) obtaining a sample from a patient exhibiting symptoms associated with IBD; (b) incubating the sample in microbe free mammal or in-vitro immune environment; (c) detecting the presence of a RORγt⁺Th cell specific nucleotide in the sample; and (d) predicting the presence or assessing status of IBD when the level of at least one RORγt⁺Th cell specific nucleotide in the patient is higher than a predetermined level of the RORγt⁺Th cell specific nucleotide.

One embodiment provides a method for diagnosing IBD in a patient by: (a) obtaining a sample from a patient exhibiting symptoms associated with IBD; (b) detecting the presence of a RORγt⁺Treg cell specific nucleotide in the sample; and (c) predicting the presence or assessing status of IBD when the level of at least one RORγt⁺Treg cell specific nucleotide in the patient is higher than a predetermined level of the RORγt⁺Treg cell specific nucleotide.

One embodiment provides a method of screening for a therapeutic composition useful for treating IBD or people at risk of IBD by: (a) identifying an individual that exhibits symptoms associated with IBD in that type of individual; (b) treating the individual with a therapeutic composition; and (d) determining whether the therapeutic composition reduces the amount of RORγt⁺Th cells present in the GI of the individual below a predetermined level.

One embodiment provides a method of screening for a therapeutic composition useful for treating IBD or people at risk of IBD by: (a) identifying an individual that exhibits symptoms associated with IBD in that type of individual; (b) treating the individual with a therapeutic composition; and (d) determining whether the therapeutic composition increases the amount of RORγt⁺Treg cells present in the GI of the individual above a predetermined level.

One embodiment provides a method of screening for a therapeutic composition useful for treating IBD or people at risk of IBD by: (a) identifying an individual that is an animal model of IBD and that exhibits symptoms associated with IBD in that individual; (b) treating the individual with a therapeutic composition; and (d) determining whether the therapeutic composition reduces the amount of RORγt⁺Th cells present in the GI of the individual below a predetermined level.

One embodiment provides a method of screening for a therapeutic composition useful for treating IBD or people at risk of IBD by: (a) identifying an individual that is an animal model of IBD and that exhibits symptoms associated with IBD in that individual; (b) treating the individual with a therapeutic composition; and (d) determining whether the therapeutic composition increases the amount of RORγt⁺Treg cells present in the GI of the individual above a predetermined level.

One embodiment provides a method of screening for a therapeutic composition useful for treating IBD or people at risk of IBD by: (a) infecting an individual that is an animal model of the human GI with bacterial cultures from individuals with IBD; (b) waiting until the individual exhibits symptoms associated with IBD; (c) treating the individual with a therapeutic composition; and (d) comparing the amount of RORγt⁺Th cells present in the GI of the infected individual to the amount of RORγt⁺Th cells in a healthy individual.

One embodiment provides a method of screening for a therapeutic composition useful for treating IBD or people at risk of IBD by: (a) infecting an individual that is an animal model of the human GI with bacterial cultures from individuals with IBD; (b) waiting until the individual exhibits symptoms associated with IBD; (c) treating the individual with a therapeutic composition; and (d) comparing the amount of RORγt⁺Treg cells present in the GI of the infected individual to the amount of RORγt⁺Treg cells in a healthy individual.

One embodiment provides a method of screening for a therapeutic composition useful for treating IBD or people at risk of IBD by: (a) identifying an animal that serves as a model of IBD and that has IBD; administering a therapeutic composition to that individual; and (b) assaying the effect of the therapeutic composition on the RORγt⁺Th cell levels in the GI of the animal.

One embodiment provides a method of screening for a therapeutic composition useful for treating IBD or people at risk of IBD by: (a) identifying an animal that serves as a model of IBD and that has IBD; administering a therapeutic composition to that individual; and (b) assaying the effect of the therapeutic composition on the RORγt$^+$Treg cell levels in the GI of the animal.

One embodiment provides a method of screening for a therapeutic composition useful for treating IBD or people at risk of IBD by: (a) administering a therapeutic composition to a patient diagnosed with IBD and (b) assaying the effect of the therapeutic composition on the levels of RORγt$^+$Th cells in the gut of the patient; (c) comparing the levels of bacterial communities in the treated patient with levels of RORγt$^+$Th cells in a healthy individual; and (d) determining whether the therapeutic composition caused levels of RORγt$^+$Th cells to reach a predetermined level in the patient.

One embodiment provides a method of screening for a therapeutic composition useful for treating IBD or people at risk of IBD by: (a) administering a therapeutic composition to a patient diagnosed with IBD and (b) assaying the effect of the therapeutic composition on the levels of RORγt$^+$Treg cells in the gut of the patient; (c) comparing the levels of strain 1687A6 in the treated patient with levels of RORγt$^+$ Treg cells in a healthy individual; and (d) determining whether the therapeutic composition caused levels of RORγt$^+$Treg cells to reach a predetermined level in the patient.

FIG. 1 shows that IBD-associated microbiotas enhance induction of gut RORγt+Th compared to healthy donor microbiotas in gnotobiotic mice. (A and B) The proportion of gut RORγt+Th varies in individual mice colonized with different donor microbiotas. Shown is the proportion of RORγt+ cells of CD4+FoxP3-. Flow cytometry plots include data acquired at different times, thus gating differs between plots. (C) The mean proportion of RORγt+Th induced in the colon, ileum, and mLN of groups of mice colonized with IBD donor microbiotas is greater than with healthy micro-biotas. (D) The correlation between the proportion of RORγt+Th induced in colon, ileum, and mLN by each microbiota. (E) The proportion of RORγt+Th and IL-17A+ CD4 T cell induced by a microbiota are correlated. (F, G and H) The mean proportion of (F) IL-17A+Th17 cells, (G) IFNγ+Th1 cells, (H) IL-22$^-$T cells induced in colon and ileum is equivalent with healthy or IBD donor microbiotas. Cells are gated as in FIG. 1A. (I) The proportion of gut GATA3+Th in individual mice colonized with different donor microbiotas. Shown is the proportion GATA3+ cells of CD4$^+$FoxP3$^-$. (J) The mean proportion of GATA3+Th induced in the colon ileum of groups of mice colonized with healthy and IBD microbiotas. (A-J) n=15 healthy, 8 UC and 7 CD microbiotas (RORγt), n=11 healthy, 6 UC and 7 CD microbiotas (IFNγ and IL-17A), n=8 healthy, 4 UC and 6 CD microbiotas (IL-22), n=10 healthy, 5 UC and 2 CD microbiotas (GATA3); (B and I) each point represents data from one mouse, in all other plots each point represents the mean value of a group of 2-12 mice colonized with a single microbiota. ns—not significant, *p<0.05, Students t-test; solid horizontal lines indicate mean±SEM, dashed horizontal lines represent the mean proportion of the cell type in germ free mice. Regression p values in (E) calculated by f-test.

FIG. 2 shows that induction of gut FoxP3+ Treg is not significantly different between mice colonized with healthy and IBD microbiotas. (A and B) The proportion of FoxP3+ Treg varies between individual mice colonized with different donor microbiotas. Shown is the proportion of FoxP3+ cells as a percentage of CD4+ T cells. Flow cytometry plots include data from different experiments, thus gating differs between plots. (C and D) The mean proportion of FoxP3+

Treg (C) and IL-10+CD4 T cells (D) induced in colon and ileum are not significantly different between healthy and IBD donor microbiotas. Shown is the proportion of FoxP3+ or IL-10+ cells as a percentage of CD4+ T cells. (E) IL-10 secretion is predominantly restricted to FoxP3+ lamina propria T cells. Shown are flow cytometry plots, gated on CD4+ T cells, representative of mice colonized with three healthy and three IBD microbiotas. (F) The proportion of gut RORγt+ Th and FoxP3+ Treg induced by different micro-biotas are not correlated. (A-E) n=11 healthy, 6 UC and 7 CD microbiotas; (B) each point represents data from one mouse, in all other plots each point represents the mean value of a group of 3-12 mice colonized with a single microbiota. ns—not significant, Students t-test; solid hori-zontal lines indicate mean±SEM, dashed horizontal lines represent the mean proportion of the cell type in germ free mice. Regression p values in (F) calculated by f test.

FIG. 3 shows that healthy donor microbiotas specifically enhance induction of gut RORγt+Treg compared to IBD-associated microbiotas. (A and B) The proportion of gut RORγt+Treg varies in individual mice colonized with dif-ferent donor microbiotas. Shown is the proportion of RORγt+ ells as a percentage of CD4+ FoxP3+ T cells. Flow cytometry plots include data from different experiments, thus gating differs between plots. (C and D) The mean proportion of RORγt+ Treg induced in the colon or ileum of groups of mice colonized with healthy donor microbiotas is greater than with IBD microbiotas (C). (D) shows data from (C), segregated according to cohort. (E) The mean propor-tion of RORγt+Treg induced in the mLN is not significantly different between groups of mice colonized with healthy or IBD donor microbiotas. (F) The proportion of RORγt+Treg induced by each microbiota is correlated between colon and ileum, but not between mLN and either gut tissue. (G) The majority of colon lamina propria T cell-derived IL-17A secretion is from FoxP3-cells. Shown are flow cytometry plots representative of at least three mice per microbiota. Gated on CD4+ RORγt+ cells; flow cytometry plots include data from different experiments, thus gating differs between plots. (A-F) n=15 healthy, 8 UC and 7 CD microbiotas; (B) each point represents data from one mouse, in all other plots each point represents the mean value of a group of 2-12 mice colonized with a single microbiota. ns—not significant, *p<0.05, p<0.01, * p<0.001, Students t-test; solid hori-zontal lines indicate mean±±SEM, dashed horizontal lines represent the mean proportion of the cell type in germ free mice. Regression p values calculated by f-test.

Figures 11A, 11B:
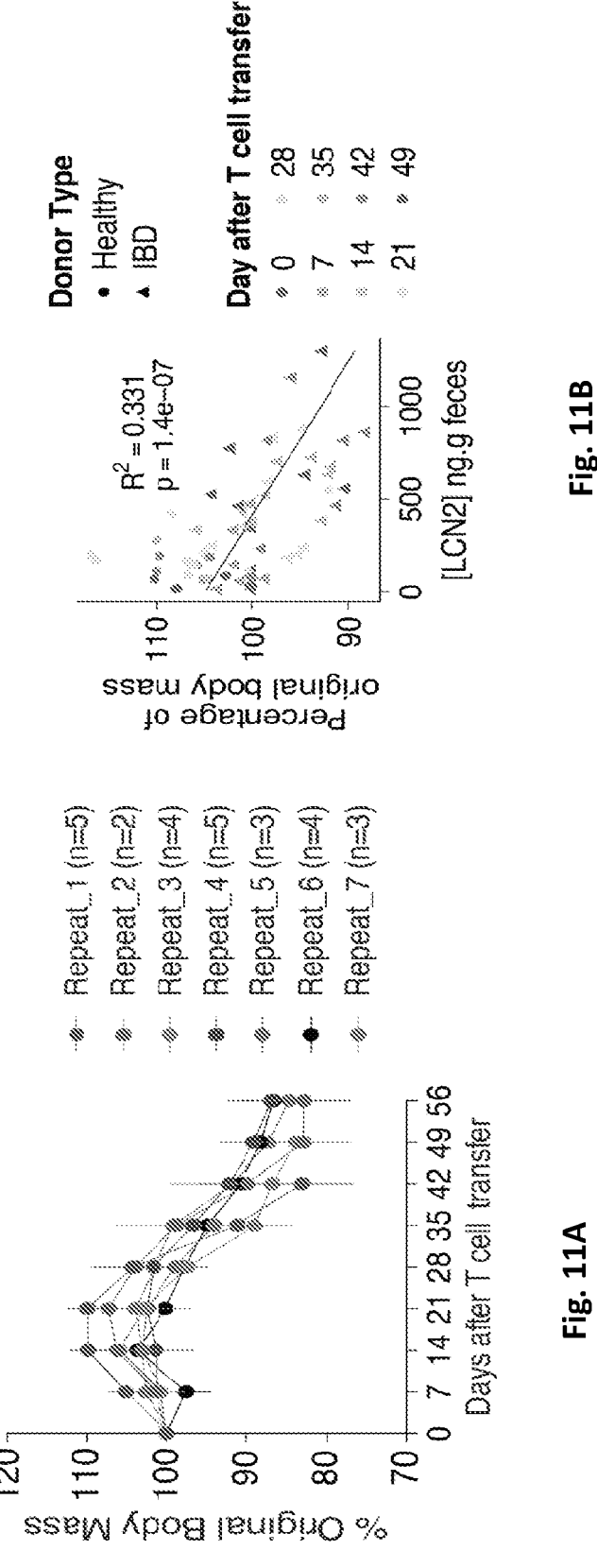
FIG. 11A-G. The figures show that IBD-associated microbiotas transmit enhanced 819 colitis severity to susceptible mice.

FIG. 4 shows that IBD-associated microbiotas transmit enhanced colitis severity to susceptible mice. Rag−/−T cell transfer (RagTCT) colitis in mice colonized with healthy or IBD donor microbiotas. (A and B) Body mass loss (A) and fecal lipocalin2 (LCN2) (B) were significantly greater in RagTCT mice colonized with IBD donor microbiotas rela-tive to healthy microbiotas. (C) Representative H&E stained colon sections from RagTCT mice colonized with different human donor microbiotas 5-7 weeks after T cell transfer. (D) Body mass loss was greater at week 6 in RagTCT mice colonized with human UC or CD microbiotas. (E and F) Exacerbated colitis severity is transferred by IBD donors from two cohorts (E) and with both stool and cultured IBD microbiotas (F). (G) The proportion of RORγt+Th and IFNγ+IL-17A+ of CD4+ T cells induced in the colon of RagTCT mice colonized with IBD donor microbiotas is greater than with healthy microbiotas 4 weeks after TCT. Each point represents data from one mouse, each color represents a different microbiota. (H) Representative flow cytometry plots demonstrating induction of RORγt+ Treg from the progeny of transferred naïve T cells in the colon lamina propria 4 weeks after TCT. Gated on CD4+ cells. (I) The proportion of FoxP3+Treg and RORγt+ Treg induced in the colon of RagTCT mice is not significantly different between IBD and healthy microbiotas 4 weeks after TCT. Each point represents data from one mouse; each color represents a different microbiota. Proportions of FoxP3+ Treg are as a percentage of CD4+ T cells and RORγt+ Treg are as a percentage of CD4+FoxP3+ (A, B) Thin lines represents the mean data from a group of 5-15 mice colonized with a single microbiota and bold lines represent the mean±SEM of all groups of mice colonized with either healthy donor or IBD donor microbiotas. (C) Scale bar=200 μm. (DG) Each point shows the mean weight change of a group of 5-15 mice 6 weeks after T cell transfer (n=16 healthy donors, n=6 CD donors, n=6 UC donors (of which 2 UC and 2 CD had active disease). P values are calculated using ANOVA with Tukey's correction for multiple comparisons (D) or Students t-test (all other panels). ns—not significant, p<0.01, *p<0.001, ****p<0.0001; Students t-test). See also: FIGS. 11 and 12 (G and I) Each point represents data from one mouse, each color represents a different microbiota.

FIG. 5 shows that homeostatic induction of RORγt+Treg and RORγt+Th predicts experimental colitis severity and human microbiota donor health. (A) RagTCT colitis severity is significantly correlated with RORγt+Th and RORγt+Treg, homeostatically induced in the colon and ileum of B6 gnotobiotic mice colonized with the same microbiota. Colitis severity is not correlated with the proportion of GATA3+ Th or FoxP3+Treg in B6 gnotobiotic mice. (B) Receiver Operating Characteristic (ROC) curves assessing the value of logistic models based on measurements made in humanized microbiota mice as binary classifiers to predict the health of the microbiota donor. (A and B) The body weight data represents the mean measurements of groups of 5-15 RagTCT mice colonized with a single human donor microbiota and the phenotyping data is the mean value of a group of 2-12 B6 mice colonized with the same single microbiota. P values are calculated by f-test.

Figure 6:
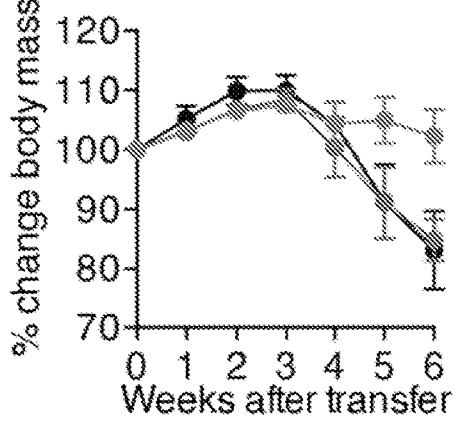
FIG. 6. The figure shows that RORγt+Treg cells are required to reduce disease severity in colitis susceptible T-cell transfer mice colonized with a healthy donor microbiota.

FIG. 6 shows that RORγt⁺Treg cells are required to reduce disease severity in colitis susceptible T-cell transfer mice colonized with a healthy donor microbiota. Specifically, a high RORγt⁺Treg inducing healthy donor microbiota (HD2021) results in less disease severity (weight loss) than that of gnotobiotic colitis susceptible mice colonized with a low RORγt⁺Treg inducing microbiota from an individual with ulcerative colitis (UC1024). This reduction in disease severity is eliminated if the T-cell transfer mice receive naïve T-cells which cannot differentiate into RORγt⁺Treg (RORγt fox×FoxP3-cre donor cells). There is no difference between the disease severity between the healthy microbiota receiving RORγt⁺Treg-deficient cells and the ulcerative colitis microbiota colonized mice receiving wildtype cells.

Figures 7A, 7B, 7C:
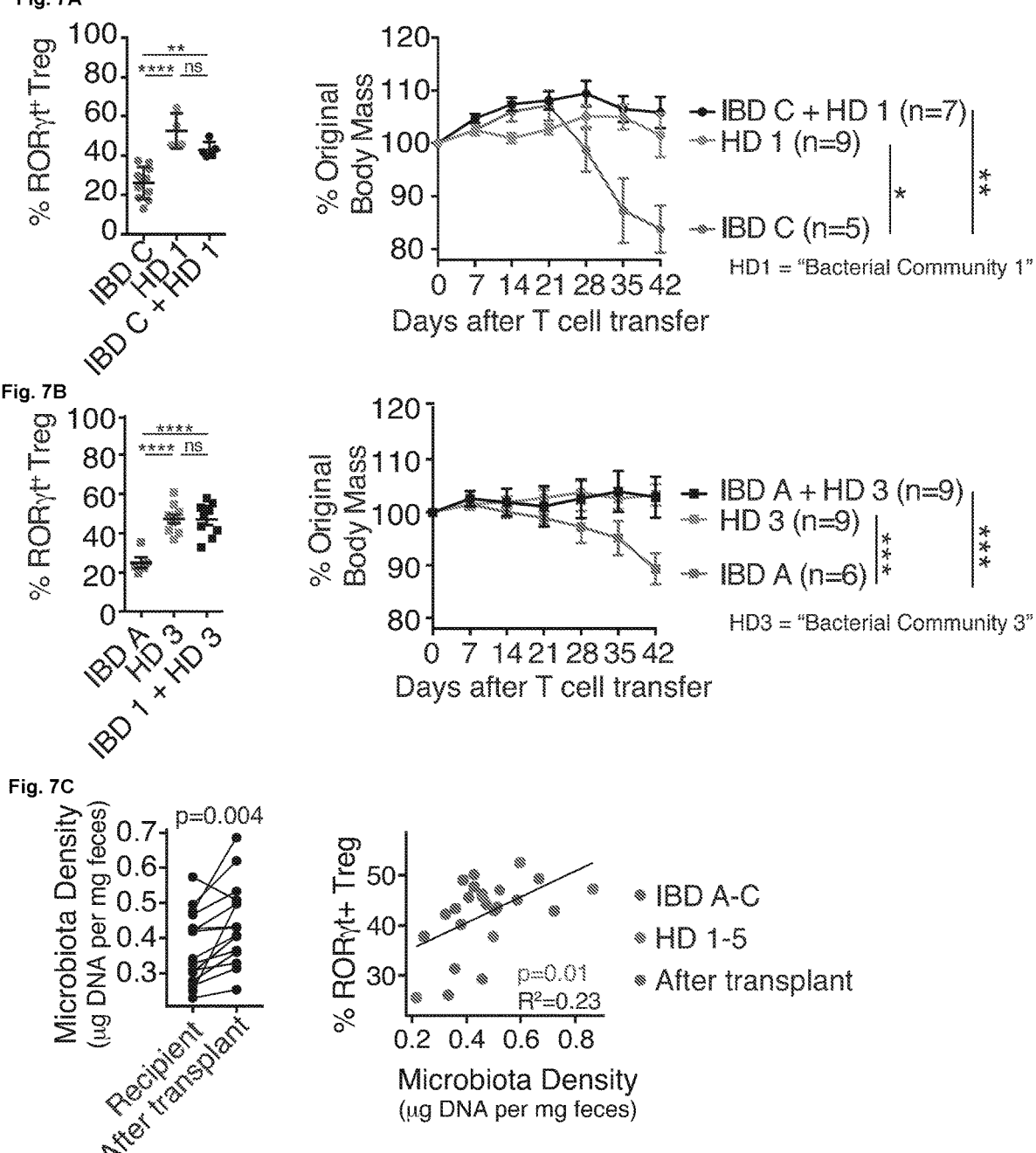
FIG. 7A-C. The figure shows that a (cultured) donor microbiota can induce colon RORγt+Treg when given as a therapeutic cocktail to a gnotobiotic mouse harboring a low RORγt+Treg inducing microbiota from an individual with IBD (data in left pane are in healthy unchallenged mice).

FIGS. 7 (A and B) shows that two (cultured) donor microbiotas can induce colon RORγt+Treg when given as a therapeutic cocktail to gnotobiotic mice harboring low RORγt+Treg inducing microbiotas from individuals with IBD (data in left panes are in healthy unchallenged mice). If the same RORγt+Treg inducing cocktails are transplanted into colitis-susceptible T-cell transfer mice harboring the low RORγt+Treg inducing IBD microbiotas, the disease pathogenesis (weight loss) is reduced in both cases. (C) shows that microbiota density increases following transplant of RORγt+Treg inducing cocktails into gnotobiotic mice harboring microbiotas from donors with IBD, and this increase in microbiota density correlates with the increase in RORγt+Treg cells in the colon.

Figure 8:
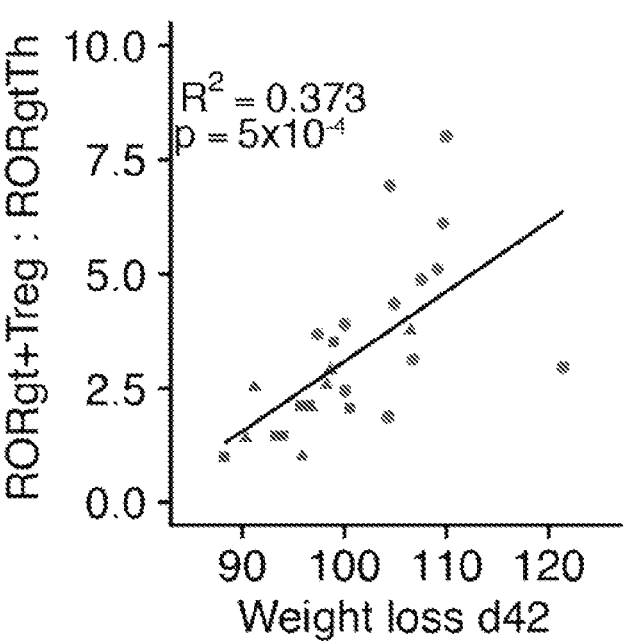
FIG. 8. The figure shows that the human microbiota-induced ratio of RORγt+Treg and RORγt+Th (Th17 cells) in unchallenged gnotobiotic mice can predict disease severity in colitis susceptible T-cell transfer mice and can predict the disease status of the human donor.

FIG. 8 shows that the human microbiota-induced ratio of RORγt⁺Treg and RORγt⁺Th (Th17 cells) in unchallenged gnotobiotic mice can predict disease severity in colitis susceptible T-cell transfer mice and can predict the disease status of the human donor. See also FIG. 5B providing the AUC.

Figures 1C, 1D, 1E, 1F:
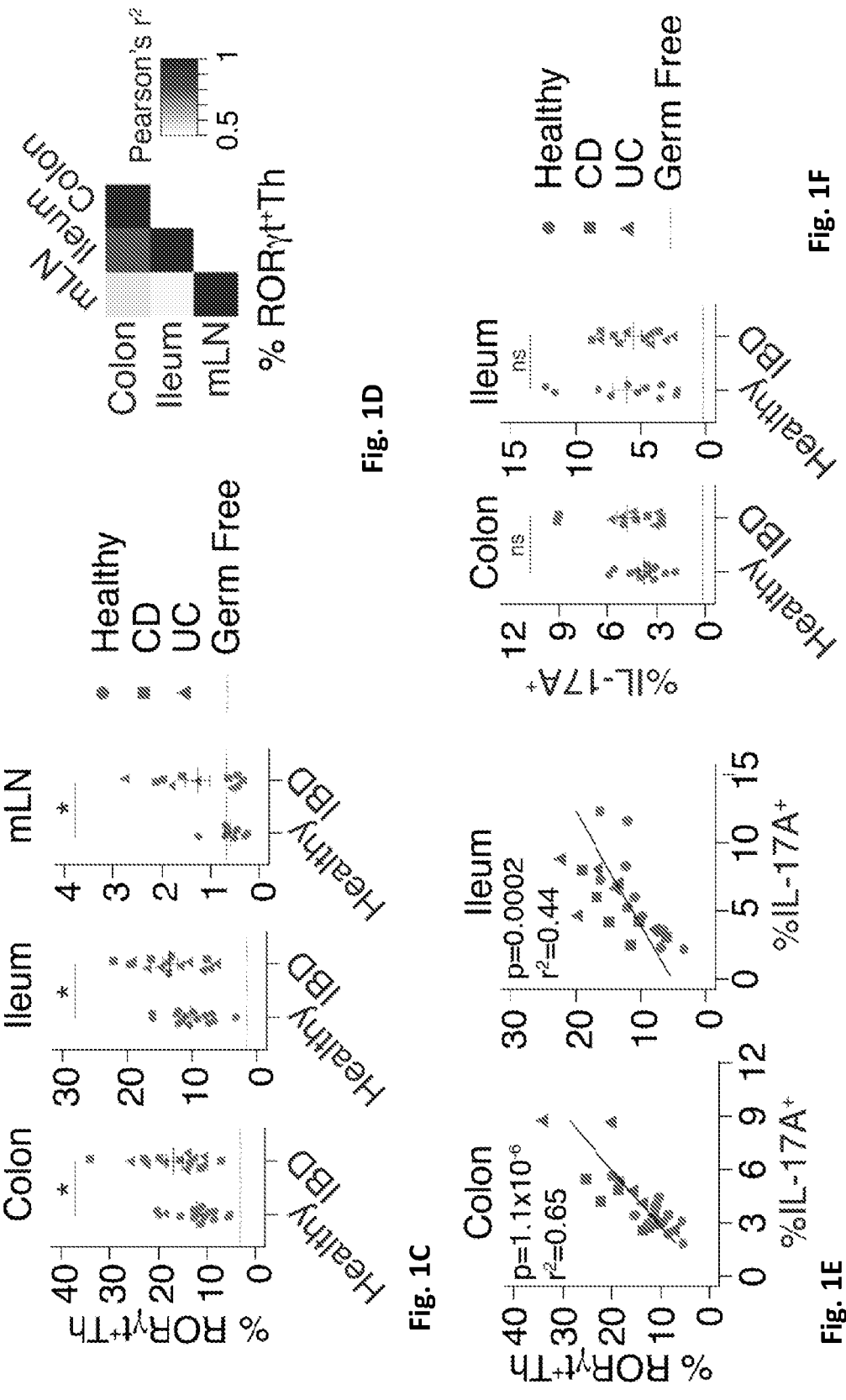
Figures 9A, 9B:
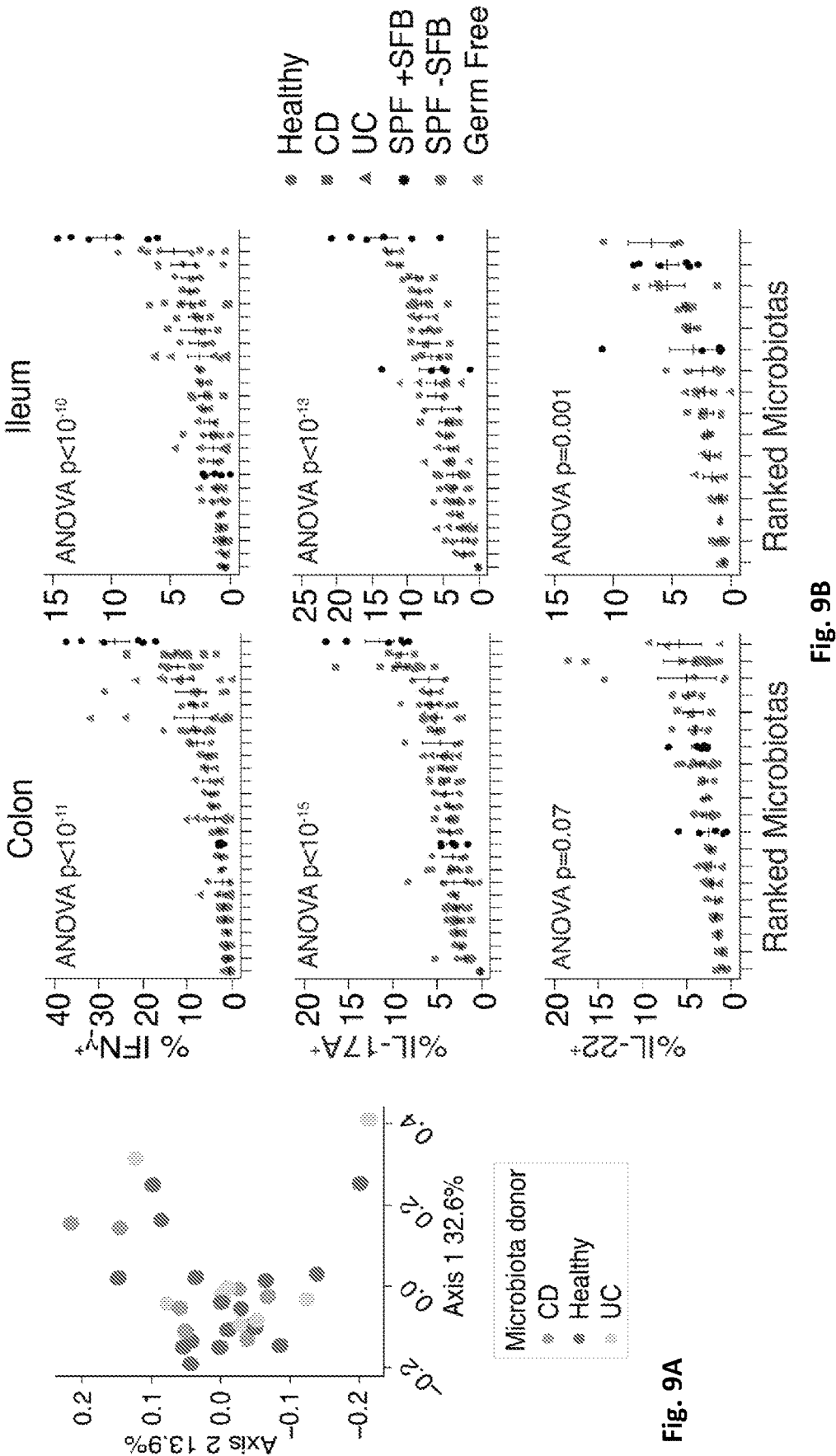
FIG. 9A-D. The figures show that the proportions of gut Thelper populations are influenced by microbiota donor.
Figures 9C, 9D:
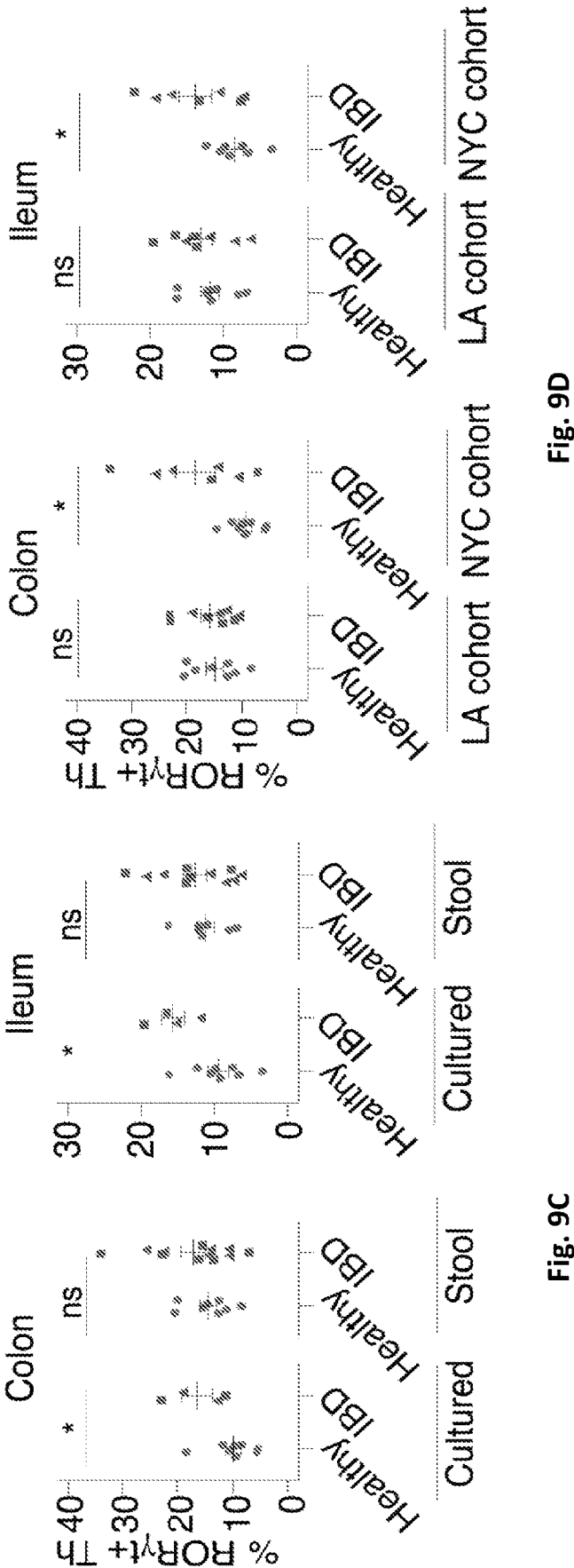

FIG. 9 shows that the proportions of gut Thelper populations are influenced by microbiota donor. (A) PCoA based on unweighted UniFrac distances of 16S rDNA amplicon sequencing of the human donor microbiotas used in this study reveal no significant disease-associated clustering. Related to Table 1. (B) The proportions of colon and ileum IFNγ+, IL-17A+ and IL-22+ CD4+ T cells are significantly influenced by the donor microbiota. Each symbol represents data from one mouse. (C) The proportion of RORγt+ Th induced by donor microbiotas in colon and ileum of B6 gnotobiotic mice colonized with either cultured collections of microbes or total stool microbiota. Each point represents the mean value of a group of 2-12 mice colonized with a single microbiota. Data is also shown in FIG. 1C, but here is segregated according to the type of microbiota inoculum. (D) The proportion of RORγt+ Th induced by donor microbiotas in colon and ileum of B6 gnotobiotic mice colonized with microbiotas from two independent cohorts of donors. Each point represents the mean value of a group of 2-12 mice colonized with a single microbiota. Data is also shown in FIG. 1C, but here is segregated according to donor cohort. (B) n=11 healthy, 6 UC and 7 CD microbiotas (IFNγ and IL-17A), n=8 healthy, 4 UC and 6 CD microbiotas (IL-22); each point represents data from one mouse. (C and D) each point represents the mean value of a group of 2-12 mice colonized with a single microbiota. ns—not significant, *p<0.05, Students t-test; horizontal lines indicate mean±SEM. See also FIG. 1.

FIG. 10 shows that healthy donor microbiotas specifically enhance induction of gut RORγt+Treg compared to IBD-associated microbiotas. (A) The proportion of RORγt+ Treg induced by donor microbiotas in colon and ileum of B6 gnotobiotic mice colonized with either cultured collections of microbes or total stool microbiota. Each point represents the mean value of a group of 2-12 mice colonized with a single microbiota. Data is also shown in FIG. 3C, but here is segregated according to the type of microbiota inoculum. (B) The mean proportion of Helios+ Treg in colon and ileum is equivalent with healthy or IBD donor microbiotas. Shown is the mean proportion of Helios+ cells as a percentage of CD4+FoxP3+ cells. (C) The mean proportion of GATA3+ Treg in colon and ileum is equivalent with healthy or IBD donor microbiotas. Shown is the mean proportion of Helios+ cells as a percentage of CD4+FoxP3+ cells. (D) Correlations between the proportions of colon and ileum FoxP3+Treg, GATA3+ Treg, Helios+Treg and RORγt+ Treg induced by different human microbiotas. (E) Induction of colon IL-22+, Csf2+ and IL-17A+ ILC3 by four different human microbiotas. Shown is the proportion of cytokine positive cells as a percentage of CD45+, CD3/CD19-, NKp46-, RORγt+ cells. Each point represents data from one mouse and each group shows data from a different microbiota. Statistical comparisons are made using data from all mice colonized with healthy or IBD microbiotas. (F) Correlations between the proportions of colon and ileum RORγt+Treg with RORγt+ Th, GATA3+Th and IFNγ+ Th induced by different human microbiotas. Each point represents the mean data from a group of 2-12 mice. (G) Expression of CD80 and CD86 on DC and macrophages/monocytes from mice colonized with representative healthy (high RORγt+Treg, low RORγt+ Th) and IBD (low RORγt+Treg, high RORγt+Th) microbiotas. DC were gated MHCII+, CD64−, CD11c+. Macrophages/monocytes (Mac/mono) were gated MHCII+, CD64+. (A-C and F) n=15 healthy, 8 UC and 7 CD microbiotas; each point represents the mean value of a group of 2-12 mice colonized with a single microbiota. (E and G) Each point represents data from a single mouse. ns—not significant, *p<0.05,  p<0.01, *p<0.0001, Students t-test (A-C, E, G) or f-test (F); solid horizontal lines indicate mean±SEM, dashed horizontal lines indicate the mean proportion of cells from a group of germ free mice. See also FIGS. 2 and 3.

FIG. 11 shows that IBD-associated microbiotas transmit enhanced 819 colitis severity to susceptible mice. (A) A group of mice colonized with donor microbiota UC1024 was included in all T cell transfer colitis experiments to assess the efficacy and consistency of colitis induction. Shown are weight loss curves for 7 groups of mice, which served as the control group for TCT experiments performed at intervals over approximately 24 months. (B) Following induction of T cell transfer colitis, loss in body mass is significantly correlated with an elevation of fecal lipocalin2. (C) Exacerbated colitis in mice colonized with IBD microbiotas can be detected early after T cell transfer. (D) IBD-associated microbiotas from two donor cohorts transmit more severe colitis to mice than healthy donor microbiotas. (E) Complete fecal microbiotas and cultured collections of bacteria from IBD donors both transmit more severe colitis to mice than equivalent microbiotas derived from healthy donors. (F) Colitis severity is equivalent in RagTCT mice colonized with IBD microbiotas from donors who have active disease or are in remission. (G) Comparison of ten donor microbiotas that were assessed for colitogenicity in mice as both stool and cultured collection. (A) Lines represent the mean±SEM of groups of mice colonized with donor UC1024. (B) Each point shows data from one mouse at one timepoint from the time of T cell transfer. (C) Each point represents the mean weight loss of a group of 5-15 mice colonized with a microbiota at the indicated time after T cell transfer. Lines represent the mean±SEM of all healthy or IBD microbiotas. (D and E) Each thin line represents the mean data from a group of 5-15 mice colonized with a single microbiota. Bold lines represent the mean±SEM of all groups of mice colonized with either a healthy donor or IBD donor microbiotas. (F) Each point represents the mean weight loss of a group of 5-15 mice colonized with a microbiota 6 weeks after T cell transfer. (G) The mean weight change of groups of 5-15 mice colonized with either the complete stool microbiota or the cultured collection.

FIG. 12 shows that the gut microbiota relative abundances are stable following colitis induction. (A) We find no significant associations of alpha diversity (defined by Shannon index) and health status of the microbiota donor. Alpha diversity is also not significantly altered six weeks after T-cell transfer. (B) There were no significant changes in the relative abundance of the five major phyla detected in feces from Rag-deficient mice colonized with healthy or IBD microbiotas before and 6 weeks after T cell transfer. Lines connect the mean proportions from the same group of mice colonized with the same microbiota. Boxplots show the median and interquartile range. Statistical comparisons by paired Student's t-test. See also FIG. 4.

FIG. 13 shows a relationship between homeostatically-induced T cell populations and colitis severity. (A-D) Homeostatically-induced (A) IL-17A+ CD4+ T cells in the colon but not the ileum of B6 gnotobiotic mice are correlated with colitis severity (as measured by weight loss) of Rag-TCT mice colonized with the same microbiotas. In contrast, the proportions of homeostatically induced (B), IFNγ+Th, (C), Helios+Treg or (D), IL-10+ CD4 T cells in the colon and ileum of B6 gnotobiotic mice are uncorrelated with colitis severity (as measured by weight loss) of RagTCT mice colonized with the same microbiotas. (A-D) Each symbol represents the mean value from a group of 3-12 mice colonized with a single microbiota. p values calculated by f-test. See also FIG. 5.

The effect of reducing or inhibiting differentiation, proliferation, or accumulation of RORγt+Th cells can be evaluated, for example, by: administering a therapeutic composition to a subject with IBD, isolating CD4-positive cells from the GI, measuring by flow cytometry the ratio of RORγt+Th cells contained in the CD4-positive cells, and comparing the post-administration RORγt+Th cell ratio to the pre-administration ratio or a predetermined level of RORγt+Th cells.

The effect of stimulating or enhancing the differentiation, accumulation, or proliferation of RORγt+Treg cells can be evaluated, for example, by: administering a therapeutic composition to a subject with IBD, isolating CD4-positive cells from the GI, measuring by flow cytometry the ratio of RORγt+Treg cells contained in the CD4-positive cells, and comparing the post-administration RORγt+Treg cell ratio to the pre-administration ratio or a predetermined level of RORγt+Treg cells.

One can determine whether the "reducing or eliminating differentiation, accumulation, or proliferation of RORγt+Th cells" is occurring, for example, by assaying the ratio of RORγt+Th cells in the T cell group of the GI, a function of RORγt+Th cells in the GI, or expression of a marker of RORγt+Th cells in the GI.

One can determine whether the "stimulating or enhancing the differentiation, accumulation, or proliferation of RORγt+ Treg cells" is occurring, for example, by assaying the ratio of RORγt+Treg cells in the T cell group of the GI, a function of RORγt+Treg cells in the GI, or expression of a marker of RORγt+Treg cells in the GI.

Methods of detecting RORγt+Th cell or RORγt+Treg cell RNA expression markers include, for example, high throughput RNA screening, northern blotting, dot blotting, and RT-PCR. Examples of methods for detecting protein markers include, for example, ELISA, radioimmunoassay, immunoblotting, immunoprecipitation, and flow cytometry.

The present disclosure can provide methods for determining the effects of a therapeutic composition by measuring the absolute amount or the ratio of RORγt+Th cells or RORγt+ Treg cells in a microbiota of an individual diagnosed with IBD, treating the individual with a therapeutic composition, and evaluating whether the absolute amount or ratio of RORγt+Th cells is reduced or of RORγt+Treg cells is increased in comparison with a base line value obtained by performing a similar evaluation on a healthy individual.

One embodiment of the present disclosure provides a method for predicting a patient's response to a therapeutic composition and provide a prognosis. The method comprises measuring the percentage or absolute amounts measuring the absolute amount or the ratio of RORγt+Th cells or RORγt+Treg cells in a microbiota of an individual diagnosed with IBD. Comparing the values to baseline values for those amounts in a healthy subject. Combining the results of the comparison with additional diagnostic information and medical history data related to the patient. Evaluating whether the patient may show a reduction in IBD after administration of a particular therapeutic composition.

EXAMPLES

Provided below are select examples of certain embodiments; however, the disclosure is not limited to these examples or the specific embodiments recited above.

The present disclosure provides methods and markers that can be used to predict the severity of IBD in humans. In particular, the present disclosure shows that individuals harboring communities that enrich tolerogenic RORγt+Treg cells are at lower risk, while those harboring communities that enrich RORγt+Treg cells are at increased risk. The inventors have further discovered a close association between microbiota-specific homeostatic RORγt+Treg cell induction and colitis severity. Furthermore, this disclosure provides microbiota compositions as a therapeutic intervention in IBD.

IBD-Associated Microbiotas Enhance Induction of Gut RORγt+ Th17 Compared to Healthy Donor Microbiotas in Gnotobiotic Mice The inventors have identified specific markers that are correlated with IBD in human gut microbiotas. To identify these markers, the inventors colonized germ free C57B1/6J mice with fecal slurries or arrayed cultured fecal microbiota collections from two independent cohorts of either related or unrelated healthy donors (n=15) or donors with IBD (n=15). See Table 1 below.

TABLE 1

Gut microbiota samples included in gnotobiotic experiments.

| Microbiota name | Donor diagnosis | Cohort | B6 immune phenotyping | TCT colitis susceptible |
|---|---|---|---|---|
| CD1001 | CD | familial | C, S | C, S |
| CD1002 | CD | familial | C | C, S |
| CD1003 | CD | familial | S | C, S |
| CD1004 | Healthy | familial | S | S |
| HD1007 | Healthy | familial | C | C |
| HD1008 | Healthy | familial | — | S |
| HD1009 | Healthy | familial | — | S |
| HD1010 | Healthy | familial | S | S |
| HD1011 | UC | familial | — | C, S |
| HD1012 | Healthy | familial | — | S |
| HD1013 | CD | familial | S | S |
| HD1014 | Healthy | familial | S | S |
| HD1015 | Healthy | familial | — | S |
| HD1016 | Healthy | familial | S | — |
| UC1024 | UC | familial | C | C, S |
| UC1025 | UC | familial | C | — |
| UC1026 | UC | familial | S | C, S |
| UC1027 | Healthy | familial | — | S |
| CD2005 | CD | non-familial | S | S |
| CD2006 | CD | non-familial | S | C, S |
| HD2017 | Healthy | non-familial | C | C |
| HD2018 | Healthy | non-familial | C, S | C |
| HD2019 | Healthy | non-familial | C | C, S |
| HD2020 | Healthy | non-familial | C | C |
| HD2021 | Healthy | non-familial | C | C, S |
| HD2022 | Healthy | non-familial | — | C |
| HD2023 | Healthy | non-familial | C | C |
| UC2028 | UC | non-familial | S | S |
| UC2029 | UC | non-familial | S | S |
| UC2030 | UC | non-familial | S | C, S |
| UC2031 | UC | non-familial | S | S |
| UC2032 | UC | non-familial | — | S |

C = gnotobiotic mice colonized with arrayed culture collection derived from donor fecal microbiota
S = gnotobiotic mice colonized with clarified fecal microbiota from donor Microbiota analysis by 16S rDNA amplicon sequencing did not distinguish between the fecal microbiotas of healthy donors and donors with CD or UC (p=0.58, PERMANOVA; FIG. 9A. Principle coordinates analysis weakly segregated the fecal microbiota of humanized microbiota mice colonized with healthy, CD or UC donor microbiotas (p=0.04, PERMANOVA, FIG. 9B).

After 4-6 weeks of colonization, the inventors profiled the intestinal lamina propria of each mouse by flow cytometry. The proportion of lamina propria RORγt+ of CD4+FoxP3− T helper cells (RORγt+Th) in colon and ileum varied significantly between donor microbiotas ($p<1\times10^{-12}$, ANOVA; FIG. 1A). Strikingly, the average proportion of RORγt+Th induced by IBD microbiotas was significantly higher than healthy donor-derived microbiotas in both colon and ileum (p=0.009 p=0.034 respectively; t-test; FIGS. 1A-C and 9). This discovery was most evident when comparing cultured microbiotas and in the cohort of unrelated donors (FIG. 10). RORγt+Th cells varied over a 6-fold range and included human microbiotas inducing similar proportions to commonly used mouse reference communities (specific pathogen free (SPF) microbiotas+/−segmented filamentous bacteria (SFB)). In addition, RORγt+ Th cells were also elevated in the mesenteric lymph node (mLN) of mice colonized with IBD microbiotas (FIG. 1C). Induction of RORγt+Th cells was highly correlated between colon and ileum, and more moderately correlated between both tissues and mLN (FIG. 1D).

The inventors found that the proportion of RORγt+Th cells was correlated with the proportion of IL-17A+ CD4 T-cells within each tissue (colon; $p=1.1\times10^{-6}$, $R^2=0.65$, ileum; $p=0.0002$, $R^2=0.44$; FIG. 1E). Although the proportion of IFNγ+ Th1, IL-22+ and IL-17A+ CD4 T cells varied by donor microbiota ($p<1\times10^{-10}$ [IFNγ and IL-17A], p=0.001 [IL-22, ileum], ANOVA) (Figure S1), the inventors discovered that these T cell subsets were not significantly altered by healthy microbiotas compared with IBD microbiotas (FIGS. 1F, 1G and 1H). In contrast, they found that the average proportion of FoxP3−GATA3+Th2 cells was higher in the colon of mice colonized with IBD microbiotas ((p<0.05, t-test); FIG. 1J).

Figure 2A:
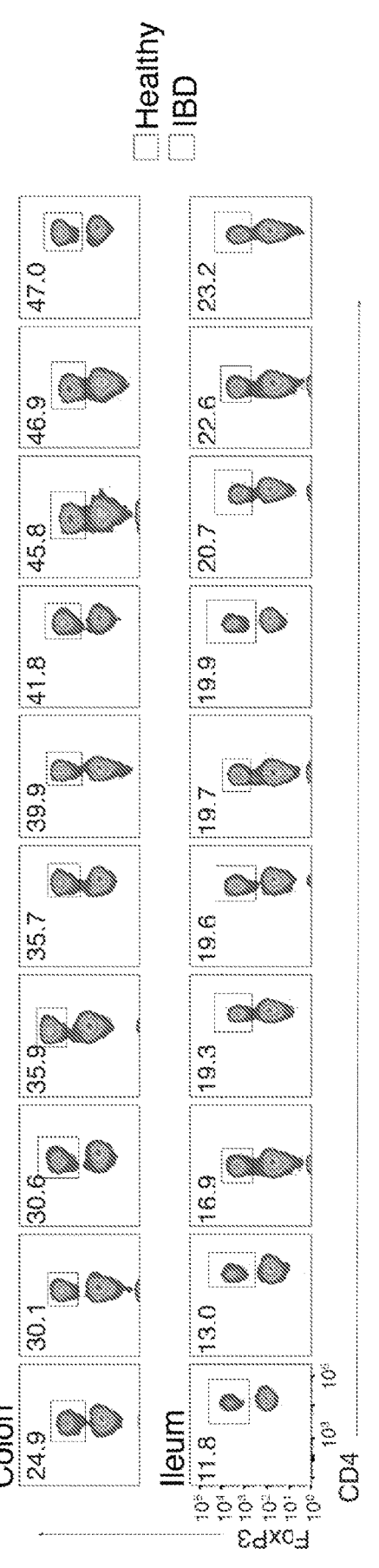
FIG. 2A-F. The figures show that induction of gut FoxP3+ Treg is not significantly different between mice colonized with healthy and IBD microbiotas.
Figures 2B, 2C, 2D, 2E:
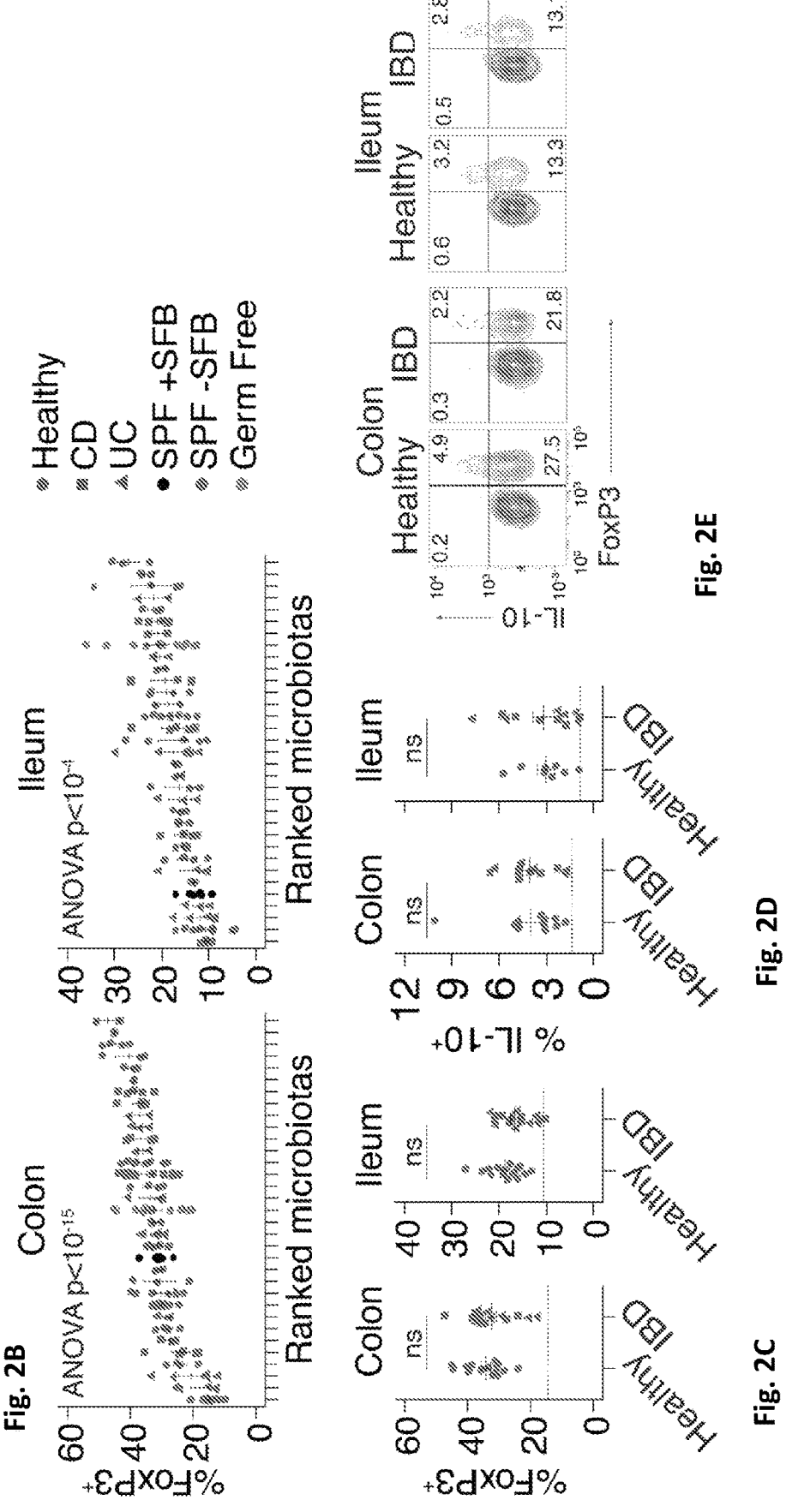
Figure 2F:
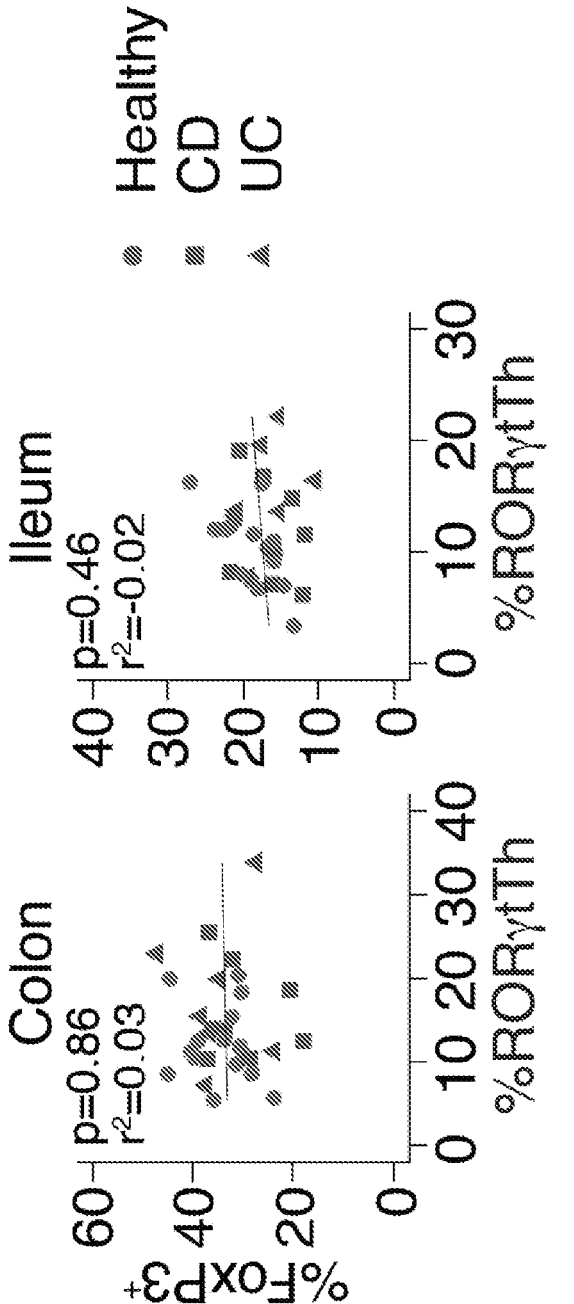

Induction of Gut FoxP3+ 102 Treg is not Significantly Different Between Mice Colonized with Healthy and IBD Microbiotas As in previous studies (Faith et al. 2014, Geva-Zatorsky et al. 2017), the majority of microbiotas led to an expansion of gut FoxP3+Treg above baseline germ-free levels (FIGS. 2A and 2B). The inventors discovered that although the proportions of FoxP3+Treg and IL-10+ CD4 T cells were significantly influenced by donor microbiota ($p<1\times10^{-15}$, p<0.0001 [FoxP3 colon, ileum], p=0.006, p=0.02 [IL-10 colon, ileum]; ANOVA), there was no observable difference between the mean proportion of FoxP3+Treg or IL-10+ CD4 T cells induced by healthy or IBD-associated microbiotas (FIGS. 2C and 2D). The majority of CD4+ T cell-derived IL-10 detected by intracellular cytokine straining was within FoxP3+ T cells (FIG. 2E). In addition, the proportion of RORγt+Th and FoxP3+ Treg induced by a microbiota were not correlated (FIG. 2F).

Figure 3A:
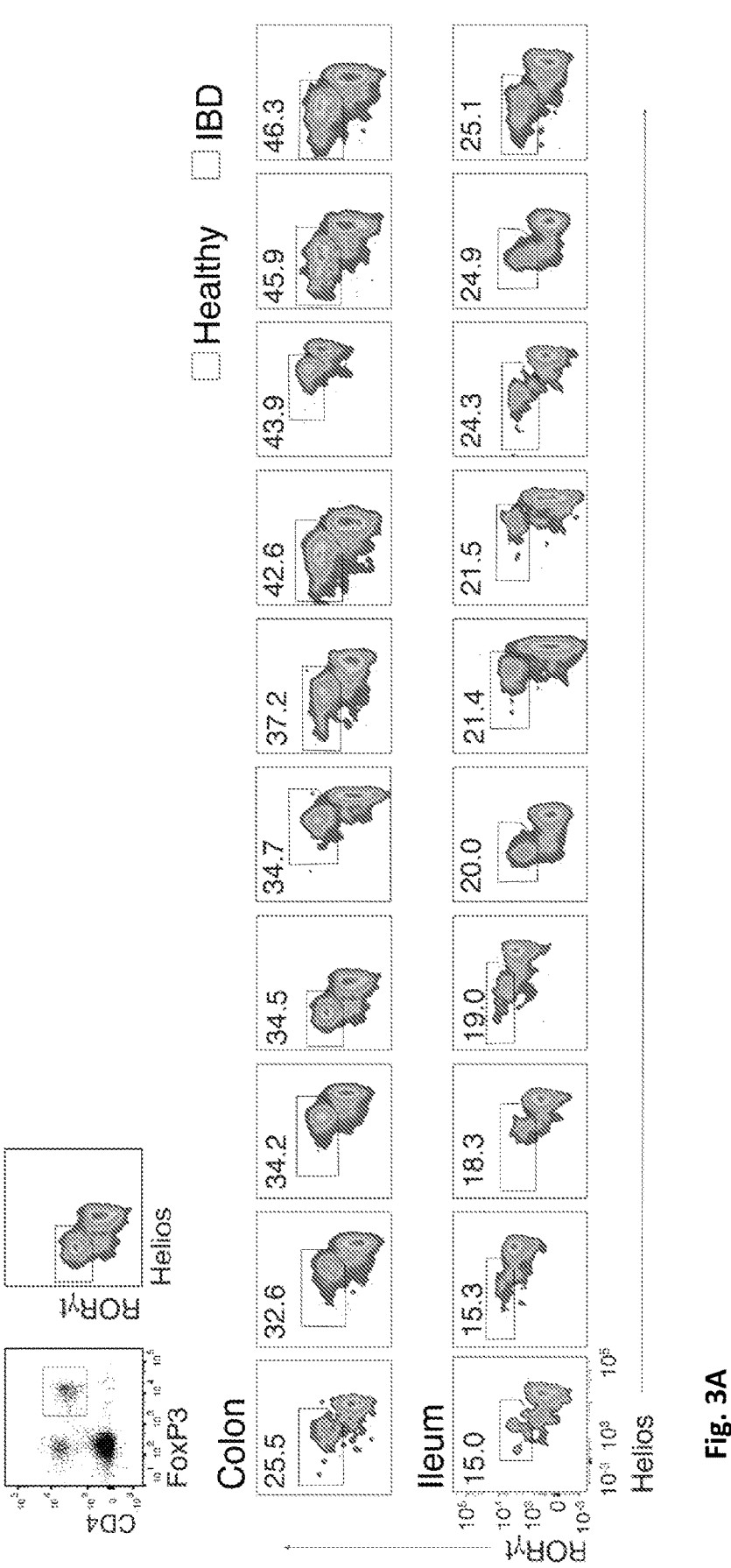
Figures 3F, 3G:
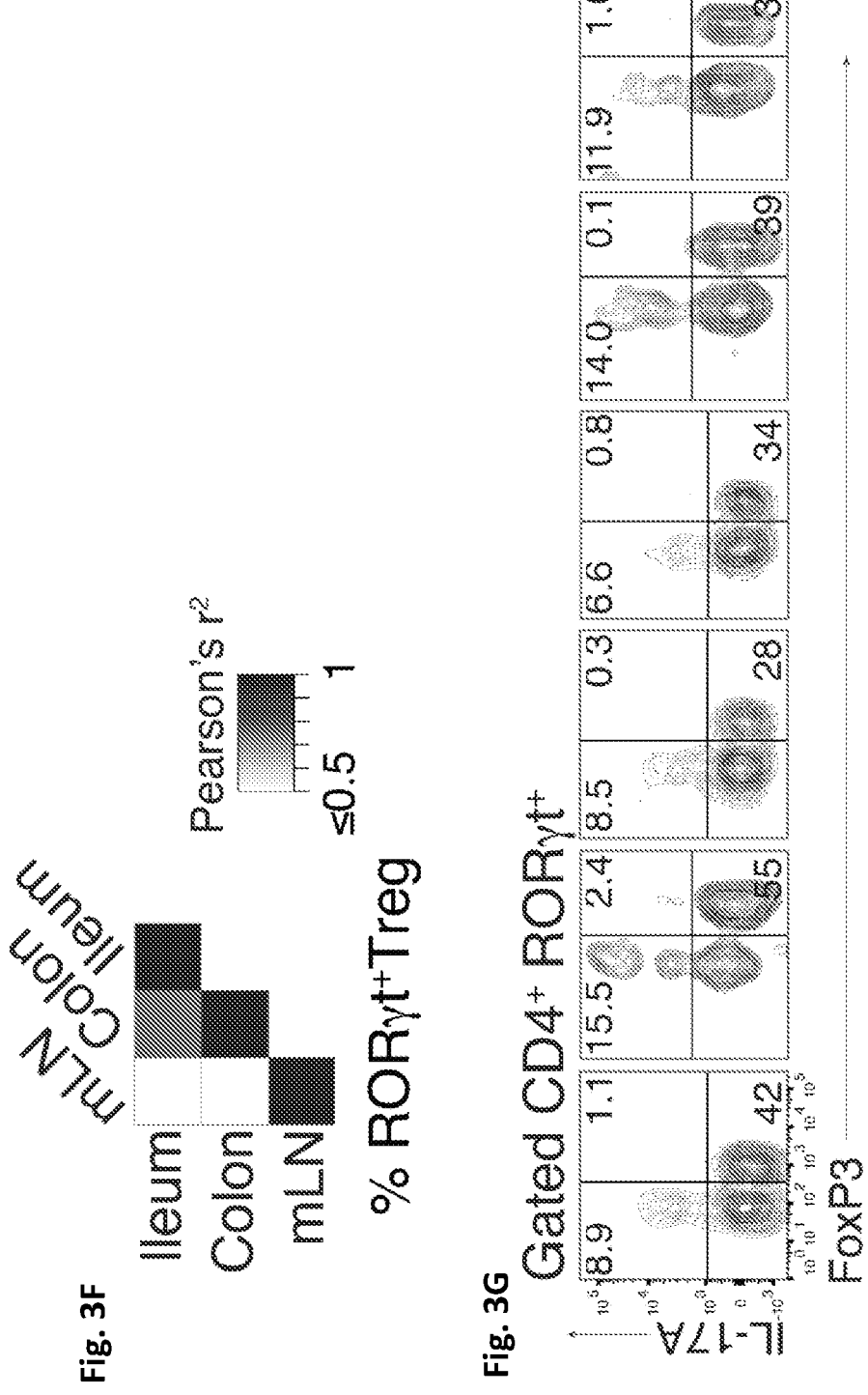

Healthy Donor Microbiotas Specifically Enhance Induction of RORγt+ Treg Compared to IBD-Associated Microbiotas Recently, the gut-specific subset of Treg that co-express FoxP3 and RORγt (RORγt+Treg) was found to be microbiota-dependent, colitoprotective and to regulate gut effector T cell responses. The inventors found that induction of RORγt+Treg in colon and ileum varied significantly with different microbiotas ($p<1\times10$-15, $p<1\times10^{-8}$ in colon and ileum, ANOVA; FIGS. 3A and 3B). In contrast to the total FoxP3+Treg population, the inventors observed a significant expansion of RORγt+Treg induced by healthy microbiotas relative to IBD microbiotas in both colon and ileum (p<0.001, t-test; FIG. 3C). This difference was significant across the two independent cohorts of microbiota donors (FIG. 3D) and in mice colonized with stool or cultured microbiotas (FIG. 10). The proportion of total FoxP3⁺Treg was correlated with RORγt⁺Treg in ileum (p<0.001; R2=0.39) and weakly correlated in colon (p=0.04, R2 128=0.1; FIG. 10D). Colonization increased the proportion of RORγt+ Treg in mLN, but there was no significant difference in the induction of mLN RORγt+ Treg by healthy or IBD microbiotas (FIG. 3E). The proportion of RORγt+ Treg in colon and ileum were correlated, but neither correlated with the proportion in mLN (FIG. 3F). Similar to previous reports in SPF mice (Sefik et al. 2015), colonic RORγt+133 Treg from mice colonized with either healthy or IBD microbiotas secreted minimal IL-17A when stimulated ex vivo compared to FoxP3-RORγt+Th (FIG. 3G).

Whereas RORgt+Treg are assumed to be induced in response to peripheral stimulus from microbiota, a large proportion of lamina propria RORγt-Treg express the transcription factor Helios, indicating a possible thymic origin (Ohnmacht et al. 2015). The inventors found that in the ileum of mice colonized with IBD microbiotas there was a greater proportion of Helios+ Treg relative to mice colonized with healthy donor microbiotas and, as expected (Sefik et al. 2015), RORγt+Treg and Helios+ Treg were inversely correlated (FIG. 10). A lower proportion of FoxP3+CD4 T cells expressed neither RORγt nor Helios (FIG. 10). This 'double negative' population was enriched in the colon mice colonized with IBD microbiotas relative to those colonized with healthy microbiotas (FIG. 10B). As previous described, FoxP3+ GATA3+ Treg were not microbiota-dependent, and they were not differentially modulated by healthy and IBD microbiotas (FIG. 10C). Cytokines secreted by type 3 innate lymphoid cells (ILC3) play roles in the maintenance of mucosal homeostasis, including Treg induction. The inventors found no significant difference in the proportion of IL-17A+, IL-22+ or Csf2+(GM- CSF+) ILC3 in colon lamina propria of mice colonized with healthy or IBD microbiotas (FIG. 10E).

It has been suggested that RORγt+Treg are uniquely positioned to regulate Th2 responses. Although the inventors observed a significant expansion of Th2 (GATA3⁺ FoxP3⁻ CD4+) cells in the colon of gnotobiotic mice colonized with IBD microbiotas relative to healthy microbiotas (p<0.05, t-test; FIG. 1I), the proportion of Th2 cells was not correlated with RORγt+ Treg (p=0.09, p=0.9 in colon and ileum, FIG. 10F). The inventors also found no correlation between the proportion of RORγt+Treg and RORγt+158 Th or IFNγ+ CD4 T cells (FIG. 10F). FoxP3-crexRORγt-flox mice, deficient in RORγt+Treg, show increased lamina propria dendritic cell (DC) activation. The inventors examined whether the deficit in RORγt+Treg observed in mice colonized with IBD microbiotas was sufficient to influence DC phenotype. In B6 mice colonized with healthy and IBD microbiotas representing the extremes of RORγt+Treg induction, the inventors found that a low proportion of RORγt+ Treg correlated with increased expression of CD80 and CD86 on CD11c⁺ CD64- DC and CD64⁺ macrophages/monocytes (FIG. 10G).

Figure 4B:
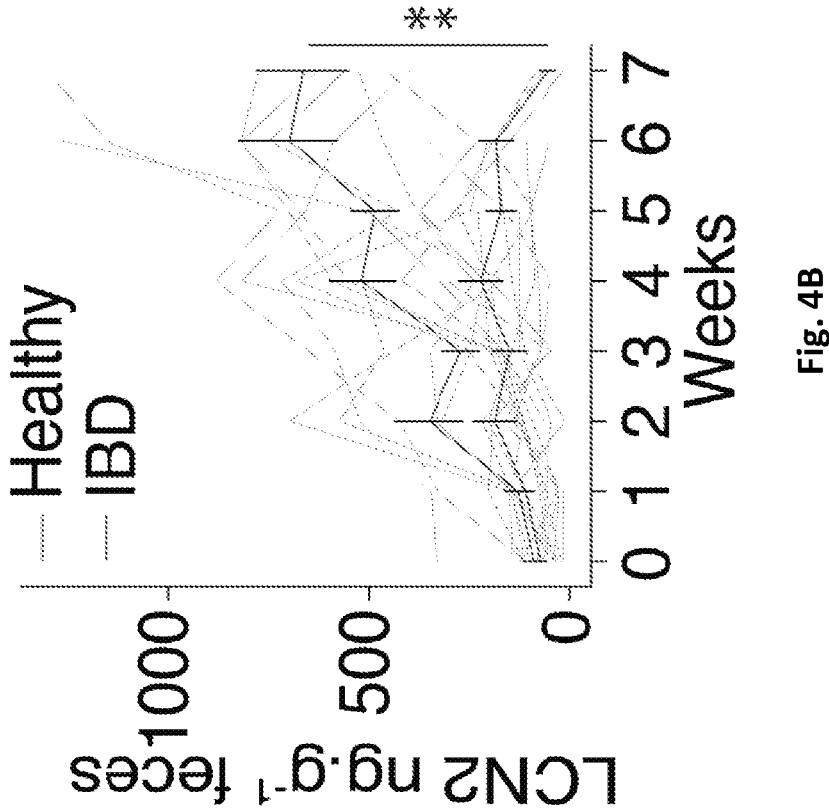
Figure 4A:
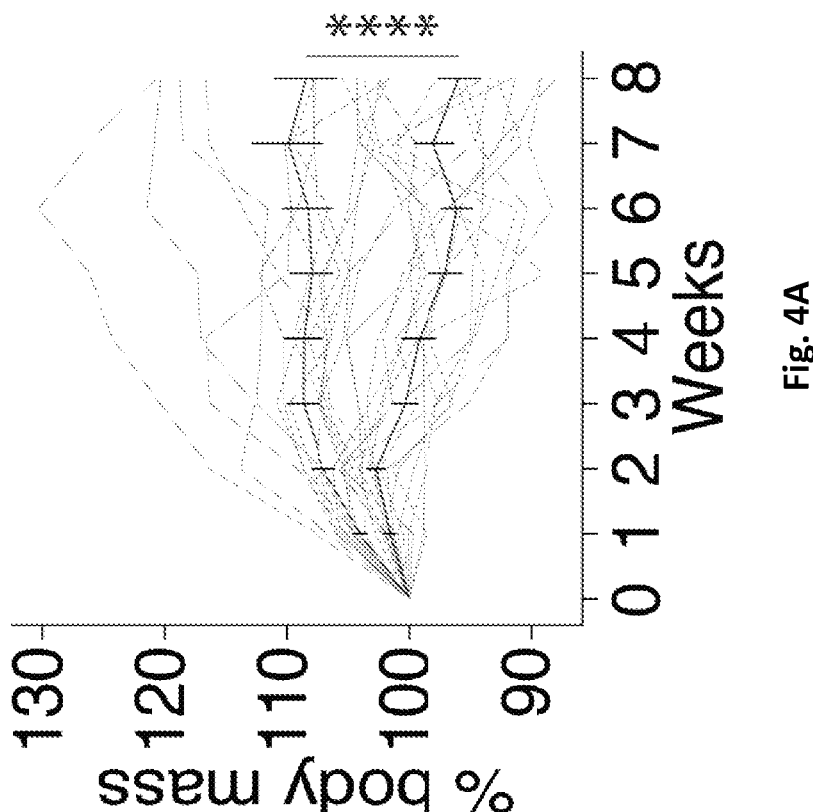
Figure 4C:
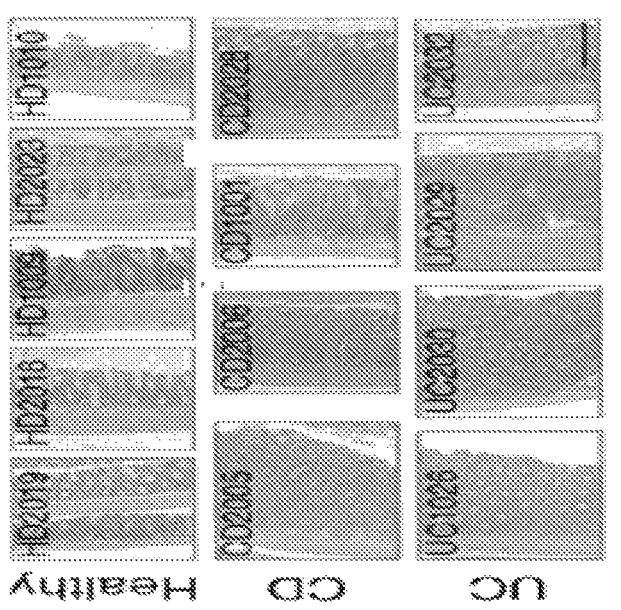

IBD-Associated Microbiotas Transmit Enhanced Colitis Severity to Susceptible Mice To assess the extent of IBD-associated microbiotas influence on colitogenesis, the inventors tested healthy- and IBD-donor microbiotas in a gnotobiotic mouse model of colitis. Given the known importance of T cells in IBD pathophysiology the inventors chose a model of colitis that is both T cell- and microbiota-dependent. Transfer of CD45RBHI (naïve) CD4 T cells to Rag deficient mice induces colitis-like pathology, but only in the presence of an immunogenic microbiota (hereafter the Rag T cell transfer, (RagTCT) model). Four-eight weeks prior to T cell transfer, the inventors colonized germ-free Rag1-/-mice with fecal microbiotas from both healthy (n=16) or IBD human donors (n=14; see Table 1). The alpha diversity (Shannon) of microbiota from B6 and Rag-/-colonized with the same human donor microbiota were significantly correlated (r²=0.6, p=0.002, f1test), an indication of similar engraftment between the mouse models. A control microbiota included in every iteration of the colitis model demonstrated low inter-experiment variation (FIG. 11A). As measured by loss in body mass, histology, and elevation of fecal lipocalin2 (LCN2), colitis was more severe in mice colonized with fecal microbiotas from individuals with IBD than those colonized with microbiotas from healthy donors (p=4.2×10– 5, p=0.0058 at day 42 for body mass and LCN2 respectively, t-test; (FIGS. 4A and 4B). Loss in body mass was correlated with elevated fecal LCN2 (R2=0.33, p=1.4×10⁻⁷; FIG. 11B).

Figure 11C:
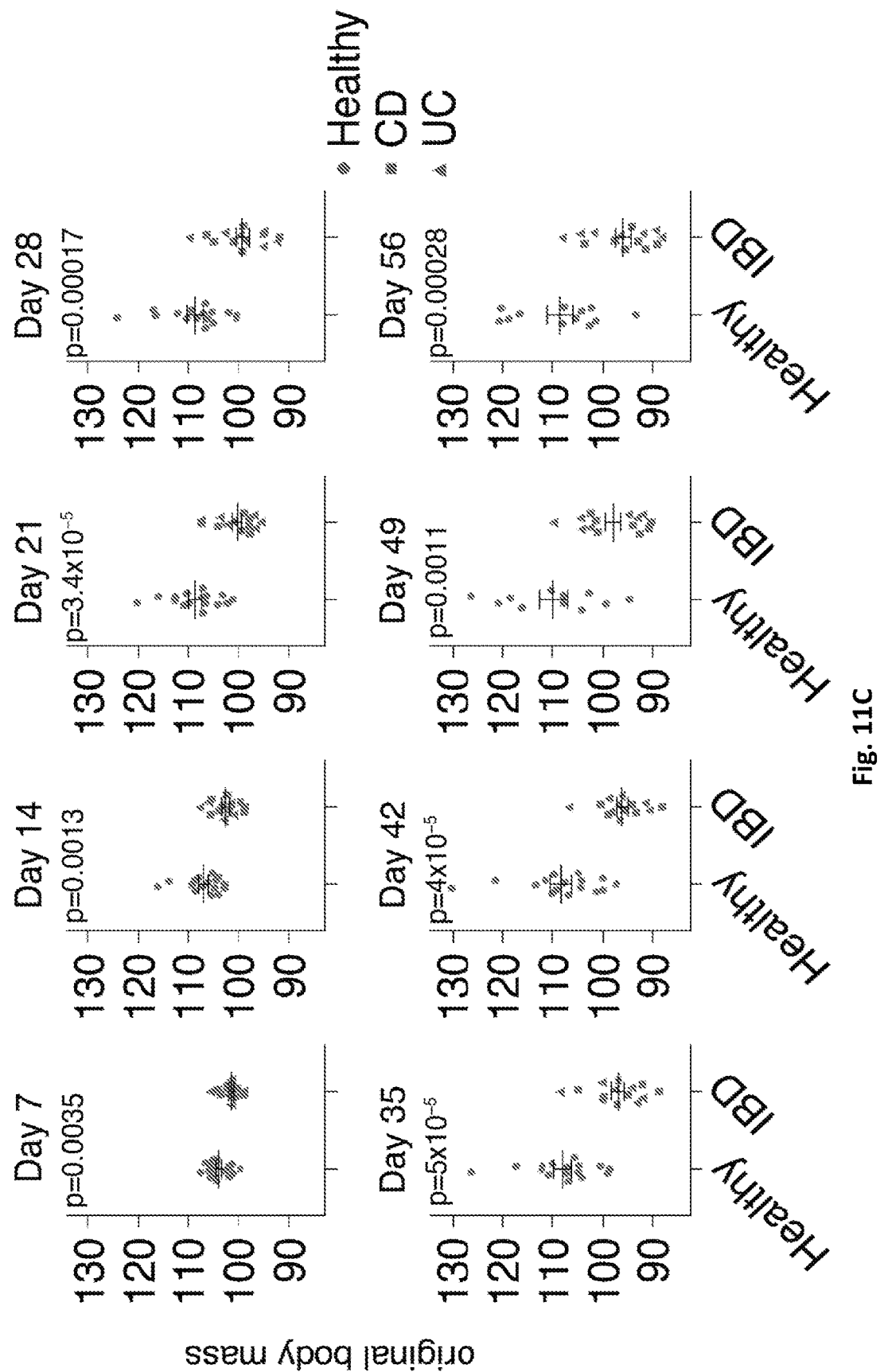
Figures 11D, 11E, 11F:
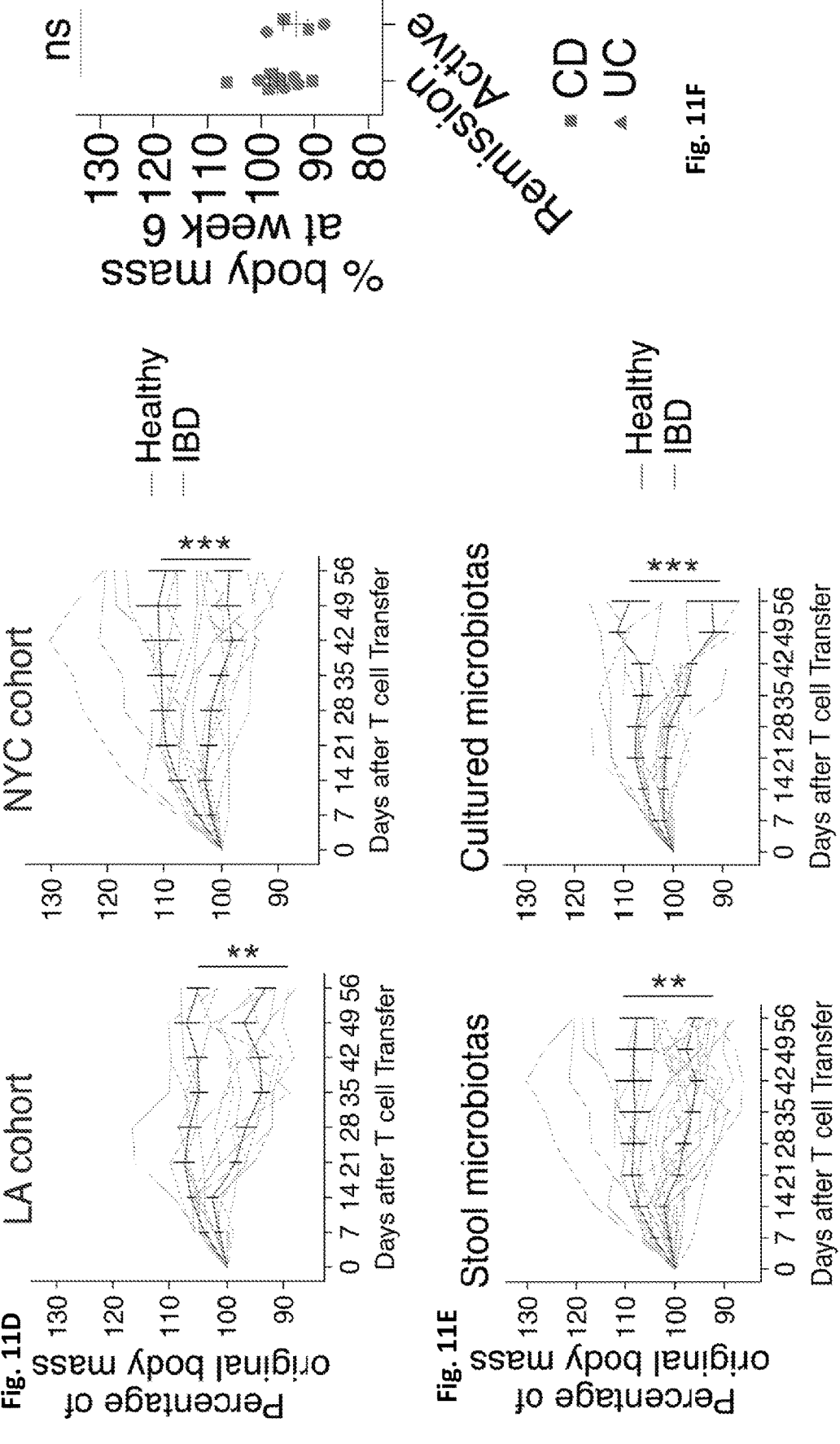
Figure 12A:
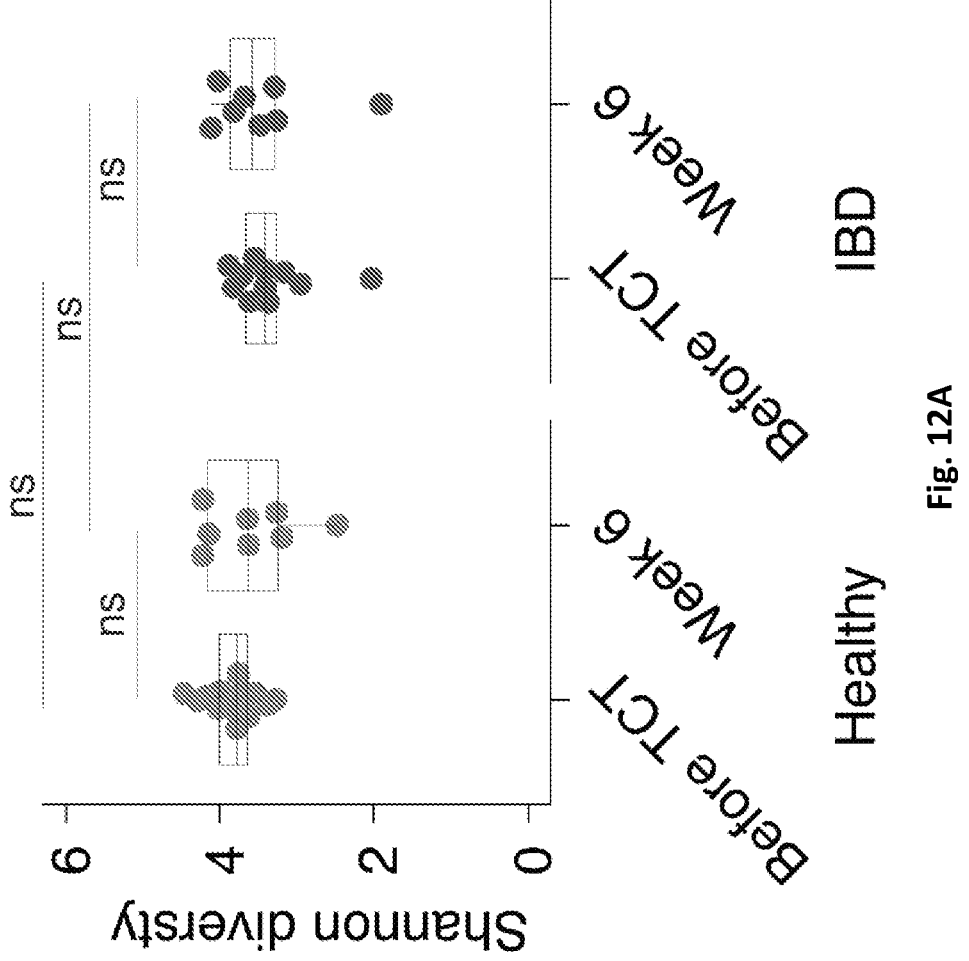
FIG. 12A-B. The figures show that the gut microbiota relative abundances are stable following colitis induction.
Figure 12B:
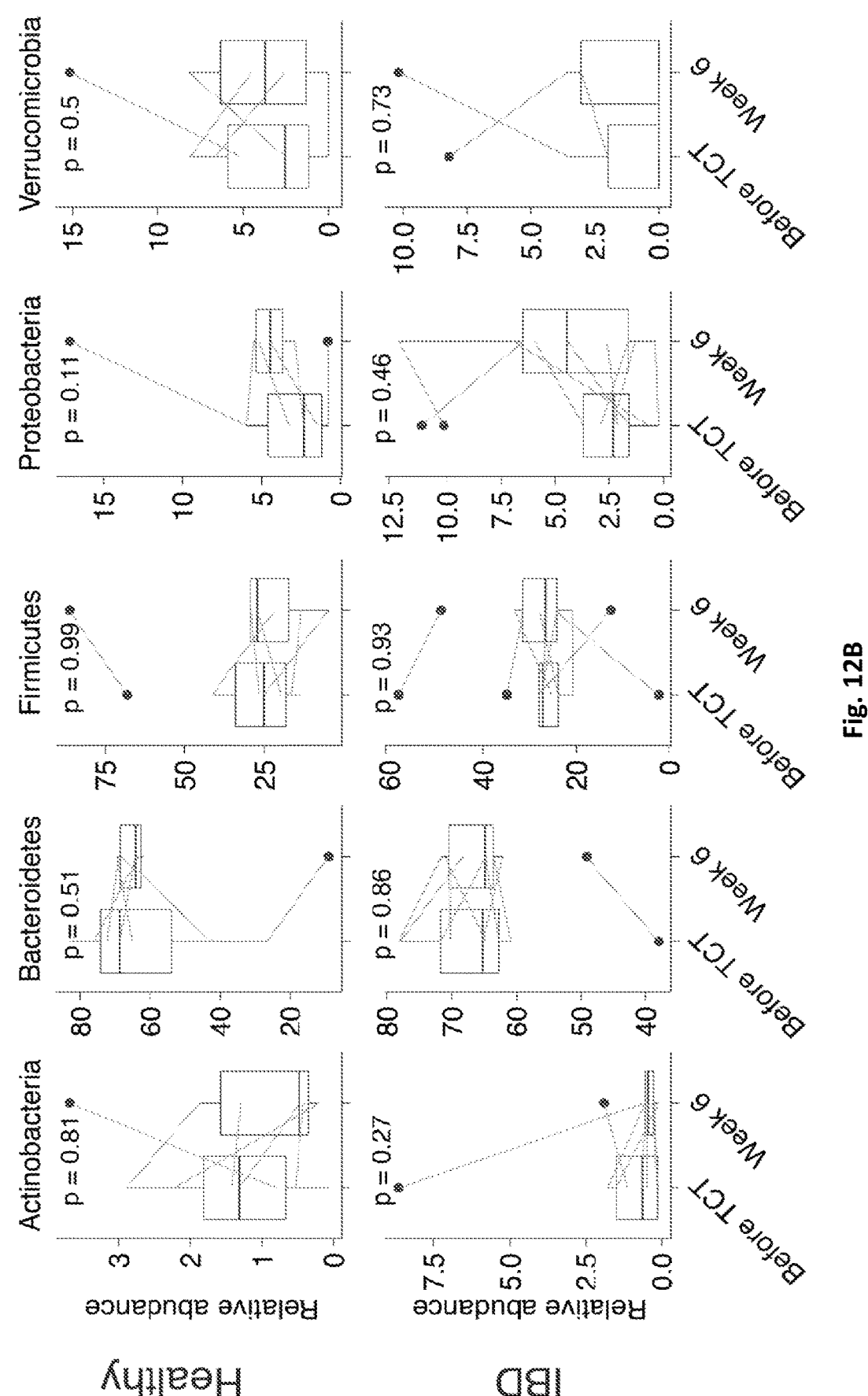

The inventors discovered that a significant difference in weight loss between healthy and IBD microbiotas was already detectable 7 days after T cell transfer and became more prominent over time (FIG. 11C). There was no significant difference in colitis severity between mice colonized with microbiotas from donors with UC compared to CD (p=0.59, t-test; FIG. 4D), and CD and UC microbiotas each independently induced colitis that was more severe than in mice colonized with healthy donor microbiotas (p<0.01, p<0.001 for UC and CD respectively, ANOVA; FIG. 4D). The inventors replicated these findings in two independent cohorts of donors (FIGS. 4E and 11D). The inventors also found both stool microbiotas and cultured collections of microbes from donors with IBD were similarly able to increase colitis susceptibility in mice, relative to healthy donor microbiotas (FIGS. 4F and 11E). Colitis was equivalent in mice colonized with IBD microbiotas from donors with active disease or in remission (FIG. 11F).

Figure 11G:
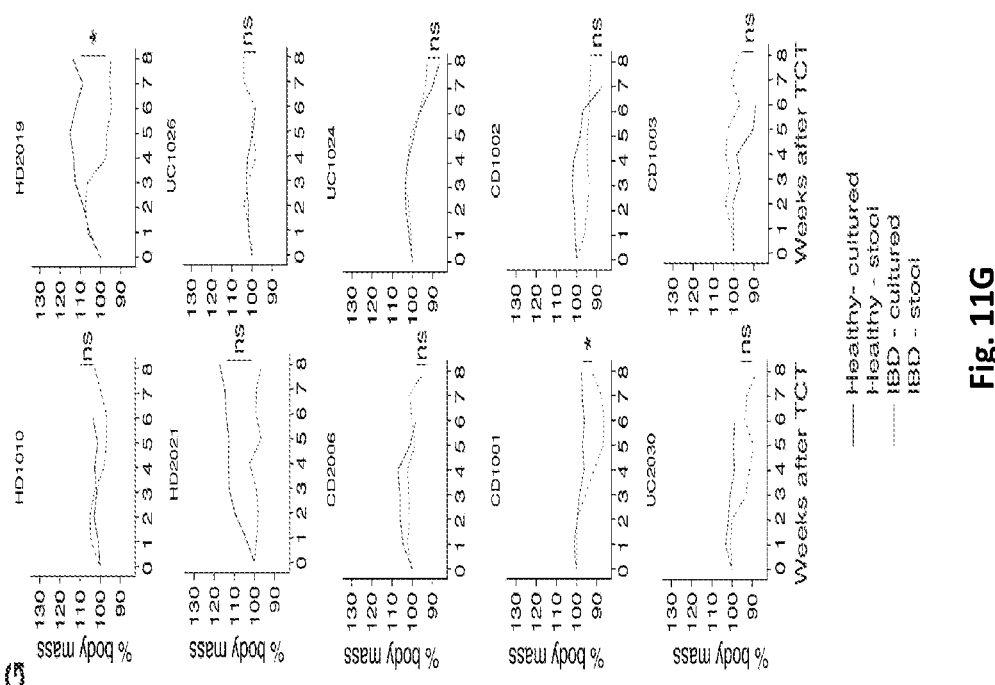

For ten donors, the inventors assayed the colitogenicity of both the stool and the cultured microbiota collection derived from the stool. Eight of the 10 cultured microbiotas transferred colitis of equivalent severity as the total stool microbiota derived from the same donor (FIG. 11G). Based on 16S rRNA amplicon sequencing, the inventors observed no difference in the alpha diversity of the engrafted healthy or IBD microbiotas or their broad taxonomic compositions, either before or after colitis induction (FIG. 12).

Figure 4I:
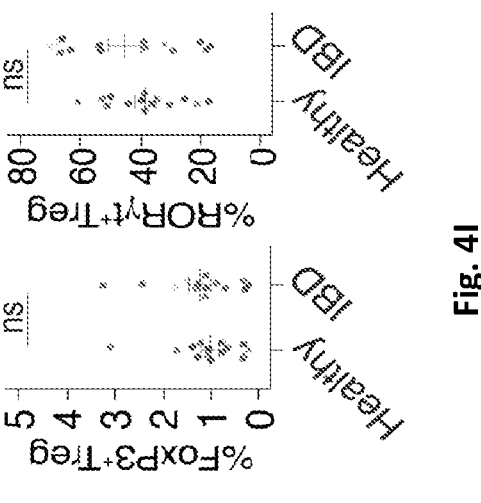
Figure 4H:
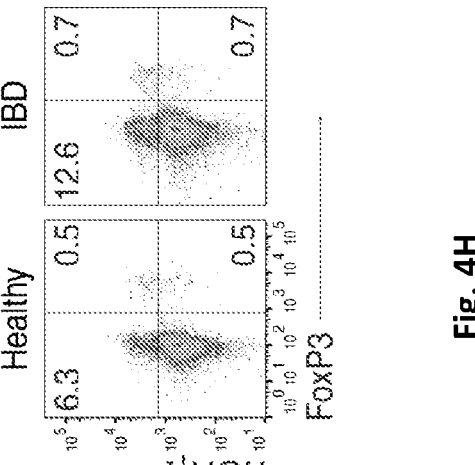
Figure 4G:
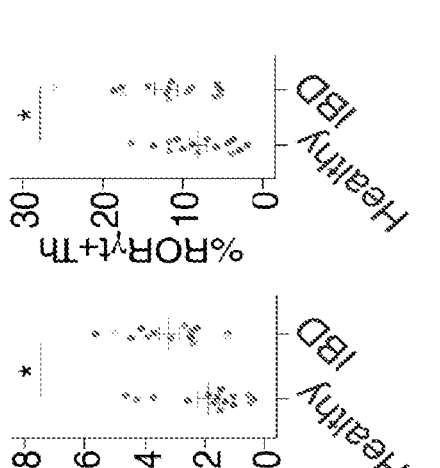

Within groups of mice colonized with one of five healthy or six IBD microbiotas, the inventors characterized the activation and differentiation of the progeny of the transferred CD45RB^{HI} T cells 4 weeks after transfer. Interpretation of immune population variation between these groups is complicated by the microbiota-induced variation in disease severity 4 weeks post-transfer. It was previously demonstrated that exacerbation of colitis in mice is associated with an increased proportion of IFNγ-IL-17A double positive CD4 T cells. In line with these observations, the inventors found the same population expanded in T-cell transfer mice colonized with the IBD microbiotas (FIG. 4G). The inventors also found an increased proportion of RORγt+Th (FoxP3⁻) in the colon of these mice (FIG. 4G). As previously reported, between 1-2% of the expanded cells in lamina propria expressed FoxP3 (FIG. 4H). This proportion was not significantly different between mice colonized with healthy or IBD microbiotas (FIG. 4I). It was notable that an average of 40-50% of the FoxP3+ cells co-expressed RORγt, indicating that the splenic origin of the naïve T cells did not hamper RORγt+ Treg development (FIGS. 4H and 4I). However, the proportion of RORγt+ Treg was highly variable between animals and there was no significant difference in the proportion of RORγt+ Treg between mice colonized with healthy or IBD microbiotas (FIG. 4I).

Figure 5A:
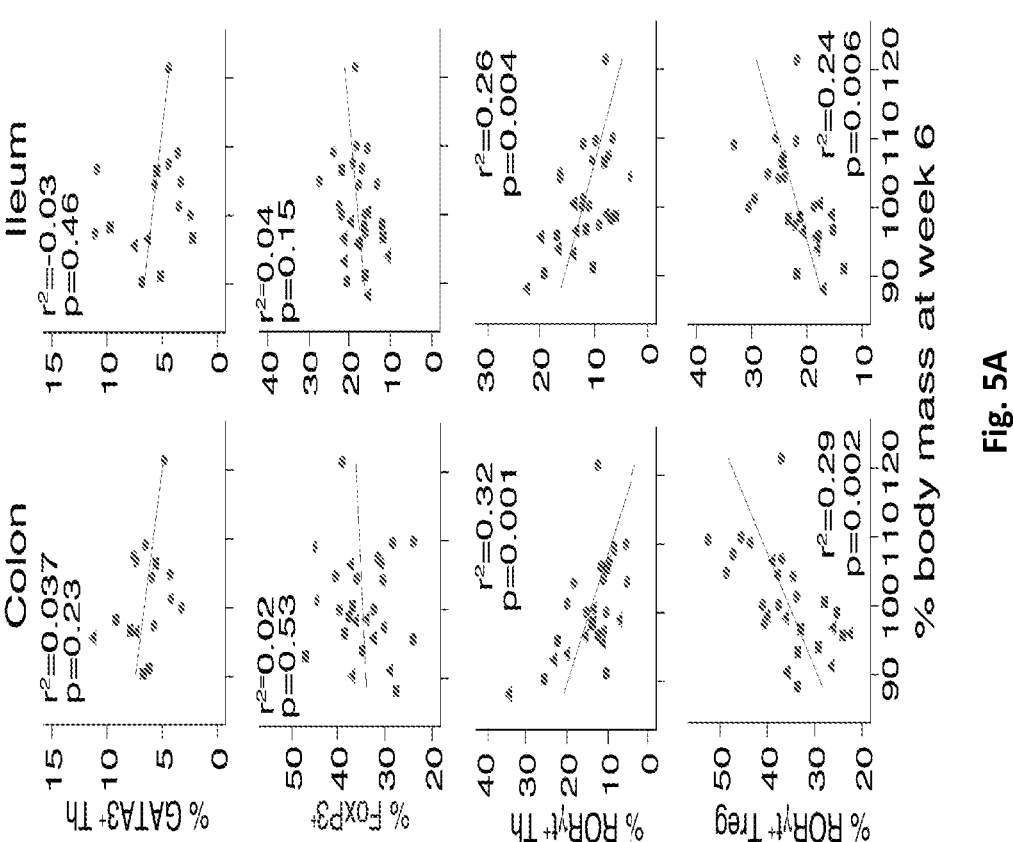
FIG. 5A-B. The figures show that homeostatic induction of RORγt+Treg and RORγt+Th predicts experimental colitis severity and human microbiota donor health.
Figure 5B:
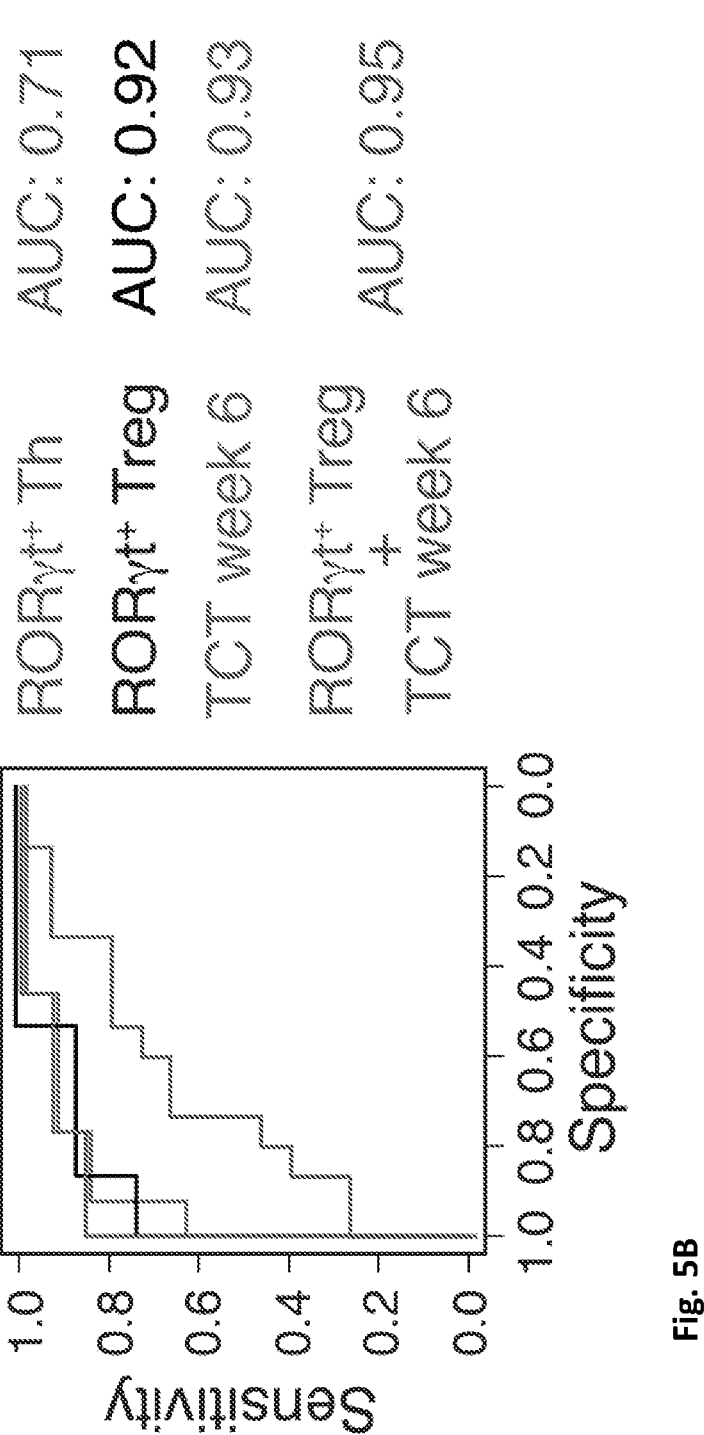

Homeostatic Induction of RORγt+Treg and RORγt+ Th Predicts Colitis Severity in Susceptible Mice Colonized with the Same Microbiota The inventors examined how the variation in CD4 T cell responses they observed in unchallenged gnotobiotic B6 mice correlated with colitis severity in RagTCT mice colonized with the same donor microbiotas. A total of 15 healthy and 14 IBD microbiotas were tested in both models (Table 1). While colitis severity was not correlated with GATA3+ Th or FoxP3+Treg (FIG. 5A), the proportion of colon and ileum RORγt+Th induced by a microbiota in B6 mice was positively correlated with colitis severity in RagTCT mice colonized with the same microbiota ($R^2$=0.32, p=0.001; $R^2$=0.26, p=0.004 for colon and ileum respectively; FIG. 5A). Induction of RORγt+ Treg in B6 mice was inversely correlated with colitis severity in RagTCT mice ($R^2$=0.29, p=0.002; $R^2$=024, p=0.006 for colon and ileum respectively; FIG. 5A). The proportion of IL-17A+ CD4 T cells induced in colon was also weakly associated with colitis severity ($R^2$=0.25, p=0.013; Figure S5). A linear model explained 53% of the variation in colitis severity (weight loss at week 6) as a function of the proportion of both RORγt+Th and RORγt+Treg in both tissues ($R^2$=0.53, p=0.002; F-test). Colitis severity was not associated with Helios+Treg, IL-10+, or IFNγ+ 237 CD4 T cells (Figure S5). Receiver Operating Characteristic (ROC) curves were used to assess the value of the humanized-microbiota mouse data in predicting the health status of the human microbiota donor using a logistic model (FIG. 5B). The proportion of colon RORγt+ Th had reasonable predictive value (AUC=0.71), but the proportion of colon RORγt+ Treg was more informative (AUC=0.92) (FIG. 5B). Colitis severity as measured by weight loss 6 weeks after T cell transfer was also highly predictive of donor health (AUC=0.93) (FIG. 5B). The inventors found the best predictive power when the proportion of colon RORγt+Treg and colitis severity at week 6 were combined in the logistic model (AUC=0.95) (FIG. 5B).

The inventors demonstrated that RORγt⁺Treg cells reduce disease severity in colitis susceptible subjects as seen in FIG. 6. Specifically, the inventors compared the effects of transferring two different types of microbiota into T-cell transfer mice. Mice receiving microbiota from a healthy individual (having high RORγt⁺Treg levels) had reduced disease severity when compared with mice that received microbiota from an individual with ulcerative colitis (and consequently low RORgtTreg levels). Moreover, this reduction in disease severity is eliminated if the T-cell transfer mice are transferred naïve T-cells that lack and cannot generate RORγt⁺ Treg. In that instance, there is no difference in disease severity between the mice receiving the healthy microbiota and those receiving the microbiota from the individual with ulcerative colitis. The severity of the symptoms are measured by percentage change in body mass of the mice over time.

The inventors have also discovered that providing RORγt+Treg-inducing microbiota as a therapeutic can reduce pathogenesis in mice harboring microbiotas from donors with IBD. FIG. 7 shows that gnotobiotic mice harboring microbiotas from two individuals with IBD (and thus low levels of RORγt+Treg) experience an improvement in symptoms after receiving a cultured microbiota that induces RORγt+Treg. The severity of the symptoms are measured by the degree of weight loss of the mice over time. The inventors have discovered that the proportion of RORγt+Treg-induced by a microbiota is proportional to the density of that microbiota (measured as the yield of microbial DNA from a known mass of stool) in the gnotobiotic mouse. FIG. 7 also shows that microbiota density is increased in gnotobiotic mice harboring microbiotas from individuals with IBD following treatment with cultured microbiotas from healthy donors, and this increase in density is correlated with the increase in RORγt+Treg cells in the colon.

Furthermore, the present disclosure shows that the ratio of RORγt⁺Treg to RORγt⁺Th17 cells in the GI is a strong predictor of disease severity. This is seen in FIG. 8, which shows that the ratio of RORγt⁺Treg to RORγt⁺Th17 cells in unchallenged gnotobiotic mice can predict disease severity in colitis susceptible T-cell transfer mice. The severity of the effects seen in the mice is a predictor of disease status in the human donor.

The inventors discovered that three bacterial communities were particularly effective in inducing RORγt⁺Treg and treating IBD in subjects. These are referred to as Communities 1, 2, and 3 in the present disclosure. The composition of the different communities are provided below.

Bacterial Community 1:

*Bacteroides_dorei*_1001099st1_G4_1001099B_141217
*Bacteroides_fragilis*_1001099st1_H1_1001099B_141217
*Bacteroides_ovatus*_1001099st1_E5_1001099B_141217
*Bacteroides_thetaiotaomicron*_1001099st1_D1_1001099B_141217
*Bifidobacterium_adolescentis*_1001099st1_F6_1001099B_141217
*Bifidobacterium_longum*_1001099st1_H2_1001099B_141217
*Bifidobacterium_longum*_1001099st2_C11_1001099B_141217
*Bifidobacterium_pseudocatenulatum*_1001099st1_G10_1001099B_141217
*Butyricicoccus*_genus_1001099st1_D10_1001099B_141217
*Clostridium*_genus_1001099st1_E2_1001099B_141217
*Collinsella_aerofaciens*_1001099st1_A1_1001099B_141217
*Escherichia_coli*_1001099st1_A12_1001099B_141217
*Lactobacillus_casei*_1001099st1_B4_1001099B_141217
*Parabacteroides_distasonis*_1001099st1_F9_1001099B_141217
*Ruminococcus_torques*_1001099st1_G7_1001099B_141217

Bacterial Community 2:

*Anaerotruncus_colihominis*_1001217st1_B4_1001217B_150727
*Bacteroides_thetaiotaomicron*_1001217st1_G7_1001217B_150727
*Bacteroides_uniformis*_1001217st1_B7_1001217B_150727
*Clostridiales*_1001217sp1_1001217st1_G3_1001217B_150727
*Clostridium_ramosum*_1001217st1_B8_1001217B_150727
*Lactobacillus_paracasei*_1001217st_F3_1001217B_150727
*Lactobacillus_rhamnosus*_1001217st1_D6_1001217B_150727

Parabacteroides_1001217sp1_1001217st1_C5_
    1001217B_150727
Ruminococcus_albus_1001217st1_F5_1001217B_
    150727
Bacterial Community 3:
Anaerofustis_stercorihominis_1001271st1_D3_
    1001271B_150615
Bacteroides_ovatus_1001271st1_H2_1001271B_150615
Bacteroides_uniformis_1001271st1_A10_1001271B_
    150615
Bacteroides_vulgatus_1001271st1_G7_1001271B_
    150615
Bifidobacterium_adolescentis_1001271st1_A4_
    1001271B_150615
Bifidobacterium_bifidum_1001271st1_H11_1001271B_
    150615
Bifidobacterium_longum_1001271st1_B4_1001271B_
    150615
Bifidobacterium_pseudocatenulatum_1001271st1_F3_
    1001271B_150615
Clostridium_1001271sp1_1001271st1_H5_1001271B_
    150615
Collinsella_aerofaciens_1001271st1_C3_1001271B_
    150615
Eubacterium_rectale_1001271st1_F12_1001271B_
    150615
Ruminococcus_obeum_1001271st1_ES_1001271B_
    150615
Bacteroides_ovatus_1001271st1_D10_1001271B_
    151109
Bacteroides_vulgatus_1001271st1_F6_1001271B_
    151109
Bifidobacterium_adolescentis_1001271st1_E2_
    1001271B_151109
Bifidobacterium_bifidum_1001271st1_F2_1001271B_
    151109

Bifidobacterium_longum_1001271st1_A6_1001271B_
    151109
Bifidobacterium_catenulatum_1001271st1_H7_
    1001271B_151109
Collinsella_aerofaciens_1001271st1_C12_1001271B_
    151109
Anaerotruncus_colihominis_1001271st1_H4_
    1001271B_151109
Bacteroides_fragilis_1001271st1_A3_1001271B_
    151109
Bacteroides_xylanisolvens_1001271st1_B2_1001271B_
    151109
Clostridium_1001271sp2_1001271st1
    D9_1001271B_151109
Clostridium_1001271sp3_1001271st1_B4_1001271B_
    151109
Coprococcus_comes_1001271st1_E1_1001271B_
    151109
Dorea_longicatena_1001271st1_G10_1001271B_
    151109
Enterococcus_faecium_1001271st1_G2_1001271B_
    151109
Enterococcus_faecium_1001271st2_G9_1001271B_
    151109
Escherichia_coli_1001271st1_H10_1001271B_151109
Eubacterium_eligens_1001271st1_F5_1001271B_
    151109
Eubacterium_siraeum_1001271st1_C8_1001271B_
    151109
Roseburia_1001271sp1_1001271st1_E4_1001271B_
    151109
Weissella_1001271sp1_1001271st1_G12_1001271B_
    151109
Weissella_1001271sp1_1001271st2_F1_1001271B_
151109

SEQUENCE LISTING

The patent contains a lengthy sequence listing. A copy of the sequence listing is available in electronic form from the USPTO web site (https://seqdata.uspto.gov/docdetail?docId=US12642819B2). An electronic copy of the sequence listing will also be available from the USPTO upon request and payment of the fee set forth in 37 CFR 1.19(b)(3).

What is claimed is:

1. A method of treating inflammatory bowel disease in a subject comprising: administering to said subject a therapeutic composition comprising a bacterial community consisting essentially of: a *Bacteroides dorei* strain, wherein said *Bacteroides dorei* strain is represented by SEQ ID NO: 4; a *Bacteroides fragilis* strain, wherein said *Bacteroides fragilis* strain is represented by SEQ ID NO: 5; a *Bacteroides ovatus* strain, wherein said *Bacteroides ovatus* strain is represented by SEQ ID NO: 7; a *Bacteroides thetaiotaomicron* strain, wherein said *Bacteroides thetaiotaomicron* strain is represented by SEQ ID NO: 10; a *Bifidobacterium adolescentis* strain, wherein said *Bifidobacterium adolescentis* strain comprising SEQ ID NO: 17; a first *Bifidobacterium longum* strain, wherein said first *Bifidobacterium longum* strain is represented by SEQ ID NO: 23; a second Bifidobacterium longum strain, wherein said second *Bifidobacterium longum* strain is represented by SEQ ID NO: 24; a *Bifidobacterium pseudocatenulatum* strain, wherein said *Bifidobacterium pseudocatenulatum* strain is represented by SEQ ID NO: 27; a *Butyricicoccus* p. strain, wherein said *Butyricicoccus* sp. strain is represented by SEQ ID NO: 29; a *Clostridium* sp. strain, wherein said *Clostridium* sp. strain is represented by SEQ ID NO: 34; a *Collinsella aerofaciens* strain, wherein said *Collinsella aerofaciens* strain is represented by SEQ ID NO: 36; a Escherichia coli strain, wherein said Escherichia coli strain is represented by SEQ ID NO: 43; a *Lactobacillus casei* strain, wherein said *Lactobacillus casei* strain is represented by SEQ ID NO: 47; a *Parabacteroides distasonis* strain, wherein said *Parabacteroides distasonis* strain is represented by SEQ ID NO: 50; and a *Ruminococcus torques* strain, wherein said *Ruminococcus torques* strain is represented by SEQ ID NO: 55.

2. The method of claim 1, wherein the therapeutic composition comprises a: vaccine, adjuvant, biological composition, pharmaceutical composition, probiotic, food, beverage, fecal transplant, bacterial composition, or a reagent used in an animal model, or a combination thereof.

3. A method of treating a disease in a subject by administering a therapeutic composition that stimulates RORyt⁺ Treg cell production in said subject, wherein said therapeutic composition comprises a bacterial community consisting essentially of: a *Bacteroides dorei* strain, wherein said *acteroides dorei* strain is represented by SEQ ID NO: 4; a Bacteroides fragilis strain, wherein said *Bacteroides fragilis* strain is represented by SEQ ID NO: 5; a *Bacteroides ovatus* strain, wherein said *Bacteroides ovatus* strain is represented by SEQ ID NO: 7; a *Bacteroides thetaiotaomicron* strain, wherein said *Bacteroides thetaiotaomicron* strain is represented by SEQ ID NO: 10; a *Bifidobacterium adolescentis* strain, wherein said *Bifidobacterium adolescentis* strain comprising SEQ ID NO: 17; a first *Bifidobacterium longum* strain, wherein said first *Bifidobacterium longum* strain is represented by SEQ ID NO: 23; a second *Bifidobacterium longum* strain, wherein said second *Bifidobacterium longum* strain is represented by SEQ ID NO: 24; a *Bifidobacterium pseudocatenulatum* strain, wherein said *Bifidobacterium pseudocatenulatum* strain is represented by SEQ ID NO: 27; a *Butyricicoccus* sp. strain, wherein said *Butyricicoccus* sp. strain is represented by SEQ ID NO: 29; a *Clostridium* sp. strain, wherein said *Clostridium* sp. strain is represented by SEQ ID NO: 34; a *Collinsella aerofaciens* strain, wherein said *Collinsella aerofaciens* strain is represented by SEQ ID NO: 36; a *Escherichia coli* strain, wherein said Escherichia coli strain is represented by SEQ ID NO: 43; a Lactobacillus casei strain, wherein said *Lactobacillus casei* strain is represented by SEQ ID NO: 47; a *Parabacteroides distasonis* strain, wherein said *Parabacteroides distasonis* strain is represented by SEQ ID NO: 50; and a Ruminococcus torques strain, wherein said *Ruminococcus torques* strain is represented by SEQ ID NO: 55.

4. The method of claim 3, wherein the disease is inflammatory bowel disease and the method comprises administering to the gastrointestinal tract (GI) of the subject said therapeutic composition.

5. The method of claim 3, wherein the therapeutic composition comprises a: vaccine, adjuvant, biological composition, pharmaceutical composition, probiotic, food, beverage, fecal transplant, bacterial composition, or a reagent used in an animal model, or a combination thereof.

6. The method of claim 4, wherein said therapeutic composition comprises a: vaccine, adjuvant, biological composition, pharmaceutical composition, probiotic, food, beverage, fecal transplant, bacterial composition, or a reagent used in an animal model, or a combination thereof.

* * * * *